(12) United States Patent
Pardridge et al.

(10) Patent No.: US 8,715,661 B2
(45) Date of Patent: *May 6, 2014

(54) METHODS AND COMPOSITIONS FOR INCREASING ARYLSULFATASE A ACTIVITY IN THE CNS

(71) Applicant: ArmaGen Technologies, Inc., Santa Monica, CA (US)

(72) Inventors: William M. Pardridge, Pacific Palisades, CA (US); Ruben J. Boado, Agoura Hills, CA (US)

(73) Assignee: Armagen Technologies, Inc., Santa Monica, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/862,250

(22) Filed: Apr. 12, 2013

(65) Prior Publication Data

US 2013/0287773 A1    Oct. 31, 2013

Related U.S. Application Data

(63) Continuation of application No. 13/609,099, filed on Sep. 10, 2012, now Pat. No. 8,486,399.

(60) Provisional application No. 61/566,497, filed on Dec. 2, 2011.

(51) Int. Cl.
*A61K 38/43* (2006.01)
*C12N 9/00* (2006.01)

(52) U.S. Cl.
USPC ...... 424/134.1; 424/94.1; 424/94.3; 435/183; 536/23.2

(58) Field of Classification Search
None
See application file for complete search history.

(56) References Cited

U.S. PATENT DOCUMENTS

| | | |
|---|---|---|
| 4,801,575 A | 1/1989 | Pardridge |
| 4,902,505 A | 2/1990 | Pardridge et al. |
| 4,946,778 A | 8/1990 | Ladner et al. |
| 5,154,924 A | 10/1992 | Friden |
| 5,180,820 A | 1/1993 | Barde et al. |
| 5,182,107 A | 1/1993 | Friden |
| 5,229,500 A | 7/1993 | Barde et al. |
| 5,438,121 A | 8/1995 | Barde et al. |

(Continued)

FOREIGN PATENT DOCUMENTS

| | | |
|---|---|---|
| EP | 0613007 A2 | 8/1994 |
| EP | 0613007 A3 | 10/1995 |

(Continued)

OTHER PUBLICATIONS

Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.

(Continued)

*Primary Examiner* — Jeffrey Stucker
*Assistant Examiner* — Adam M Weidner
(74) *Attorney, Agent, or Firm* — Wilson, Sonsini, Goodrich & Rosati

(57) ABSTRACT

Provided herein are methods and compositions for treating a subject suffering from a deficiency in arylsulfatase A in the CNS. The methods include systemic administration of a bifunctional fusion antibody comprising an antibody to a human insulin receptor and an arylsulfatase A.

26 Claims, 15 Drawing Sheets

(56) References Cited

U.S. PATENT DOCUMENTS

| | | |
|---|---|---|
| 5,453,361 A | 9/1995 | Yancopoulos et al. |
| 5,527,288 A | 6/1996 | Gross et al. |
| 5,527,527 A | 6/1996 | Friden |
| 5,562,903 A | 10/1996 | Co et al. |
| 5,610,279 A | 3/1997 | Brockhaus et al. |
| 5,618,920 A | 4/1997 | Robinson et al. |
| 5,656,284 A | 8/1997 | Balkin |
| 5,672,683 A | 9/1997 | Friden et al. |
| 5,693,762 A | 12/1997 | Queen et al. |
| 5,824,782 A | 10/1998 | Holzer et al. |
| 5,837,231 A | 11/1998 | Low et al. |
| 5,848,991 A | 12/1998 | Gross et al. |
| 5,977,307 A | 11/1999 | Friden et al. |
| 5,997,501 A | 12/1999 | Gross |
| 6,015,662 A | 1/2000 | Hackett |
| 6,041,775 A | 3/2000 | Century |
| 6,060,069 A | 5/2000 | Hill et al. |
| 6,153,190 A | 11/2000 | Young et al. |
| 6,165,783 A | 12/2000 | Weiss et al. |
| 6,248,262 B1 | 6/2001 | Kubotera et al. |
| 6,284,262 B1 | 9/2001 | Place |
| 6,287,792 B1 | 9/2001 | Pardridge et al. |
| 6,322,808 B1 | 11/2001 | Trautman et al. |
| 6,329,508 B1 | 12/2001 | Friden |
| 6,348,210 B1 | 2/2002 | Gale |
| 6,361,760 B1 | 3/2002 | Murata |
| 6,372,250 B1 | 4/2002 | Pardridge |
| 6,375,975 B1 | 4/2002 | Modi |
| 6,531,309 B1 | 3/2003 | Hu et al. |
| 6,582,945 B1 | 6/2003 | Raso |
| 6,583,272 B1 | 6/2003 | Bailon |
| 6,709,833 B2 | 3/2004 | Fukul et al. |
| 6,743,427 B1 | 6/2004 | Schenk |
| 6,858,206 B2 | 2/2005 | Kakkis |
| 7,053,202 B2 | 5/2006 | O'Keefe et al. |
| 7,078,376 B1 | 7/2006 | Thompson |
| 7,214,658 B2 | 5/2007 | Tobinick |
| 7,226,758 B1 | 6/2007 | Lin et al. |
| 7,294,704 B2 | 11/2007 | Simone et al. |
| 7,309,687 B1 | 12/2007 | Brines et al. |
| 7,388,079 B2 | 6/2008 | Pardridge et al. |
| 2002/0052311 A1 | 5/2002 | Solomon et al. |
| 2002/0137684 A1 | 9/2002 | Tchistiakova et al. |
| 2002/0169109 A1 | 11/2002 | Plata-Salaman et al. |
| 2003/0129186 A1 | 7/2003 | Beliveau et al. |
| 2003/0165853 A1 | 9/2003 | Partridge et al. |
| 2004/0072291 A1 | 4/2004 | Carr et al. |
| 2004/0101904 A1 | 5/2004 | Pardridge et al. |
| 2004/0102369 A1 | 5/2004 | Wu et al. |
| 2004/0229250 A1 | 11/2004 | Figura et al. |
| 2004/0248197 A1 | 12/2004 | Holtzman et al. |
| 2005/0142141 A1 | 6/2005 | Pardridge |
| 2007/0081992 A1 | 4/2007 | Pardridge et al. |
| 2007/0082380 A1 | 4/2007 | Pardridge et al. |
| 2007/0275882 A1 | 11/2007 | Meijer et al. |
| 2007/0280940 A1 | 12/2007 | Winkles et al. |
| 2008/0003211 A1* | 1/2008 | Fogh et al. .................... 424/94.6 |
| 2008/0051564 A1 | 2/2008 | Pardridge et al. |
| 2008/0152645 A1 | 6/2008 | Pardridge et al. |
| 2008/0170994 A1 | 7/2008 | Pardridge et al. |
| 2008/0171055 A1 | 7/2008 | Pardridge et al. |
| 2008/0292639 A1 | 11/2008 | Shen et al. |
| 2009/0053219 A1 | 2/2009 | Pardridge et al. |
| 2009/0068206 A1 | 3/2009 | Pardridge et al. |
| 2009/0156498 A1 | 6/2009 | Pardridge et al. |
| 2009/0238789 A1 | 9/2009 | Guyon et al. |
| 2010/0077498 A1 | 3/2010 | Pardridge |
| 2010/0098693 A1 | 4/2010 | Pardridge |
| 2010/0172919 A1 | 7/2010 | Grimm et al. |
| 2010/0261647 A1 | 10/2010 | Pardridge et al. |
| 2010/0290985 A1 | 11/2010 | Pardridge et al. |
| 2011/0110935 A1 | 5/2011 | Pardridge et al. |
| 2012/0269807 A1 | 10/2012 | Pardridge et al. |
| 2013/0142794 A1 | 6/2013 | Pardridge et al. |

FOREIGN PATENT DOCUMENTS

| | | |
|---|---|---|
| JP | 6-228199 | 8/1994 |
| WO | WO 99/00150 A2 | 1/1999 |
| WO | WO 99/00951 A1 | 1/1999 |
| WO | WO 99/00150 A3 | 4/1999 |
| WO | WO 99/66951 A1 | 12/1999 |
| WO | WO 00/15759 A1 | 3/2000 |
| WO | WO 03/074081 A1 | 12/2003 |
| WO | WO 2004/050016 A2 | 6/2004 |
| WO | WO 2006/081171 A1 | 8/2006 |
| WO | WO 2007/022416 A2 | 2/2007 |
| WO | WO 2007/044323 A2 | 4/2007 |
| WO | WO 2007/022416 A3 | 5/2007 |
| WO | WO 2008/022349 | 2/2008 |
| WO | WO 2009/018122 | 2/2009 |
| WO | WO 2007/044323 A3 | 5/2009 |
| WO | WO 2009/070597 A2 | 6/2009 |

OTHER PUBLICATIONS

Ai, et al., 2003. Intraputamenal Infusion of GDNF in Aged Rhesus Monkeys: Distribution and Dopaminergic Effects. The Journal of Comparative Neurology 461: 250-261.

Airavaara, et al. Effects of repeated morphine on locomotion, place preference and dopamine in heterozygous glial cell line-derived neurotrophic factor knockout mice. Genes Brain Behav. Apr. 2007;6(3):287-98.

Al Sawaf, et al. Neurological findings in Hunter disease: pathology and possible therapeutic effects reviewed. J Inherit Metab Dis. Aug. 2008:31(4):473-80.

Albayrak, et al. Effect of transient focal ischemia on blood-brain barrier permeability in the rat: Correlation to Cell Injury. Acta Neuropathol 1997;94:158-63.

Alberts, et al. Molecular Biology of the Cell. 3rd Edition. Garland Publishing Inc. New York. 1994; pp. 1206-1207.

Altsciiul, et al. Optimal sequence alignment using affine gap costs. Bulletin of Mathematical Biology. 1986; 48(5-6):603-16.

Altschul, et al. Basic Local Alignment Search Tool. J. Mol. Biol. 1990;215:403-410.

Altschul, et al. Gapped BLAST and PSI-BLAST: a new generation of protein database search programs. Nucleic Acids Res. 1977;25:3389-402.

Arndt, et al. Generation of a highly stable, internalizing anti-CD22 single-chain Fv fragment for targeting non-Hodgkin's lymphoma. Int J Cancer. Dec. 10, 2003;107(5):822-829.

Ausubel, et al. Current Protocols in Molecular Biology. John Wiley & Sons, New York, 1995 supplement.

Bachis, et al. 2003. Brain-Derived Neurotropic Factor Inhibits Human Immunodeficiency Virus-1/gp 120-Mediated Cerebellar Granule Cell Death by Preventing gp 120 Internalization. The Journal of Neuroscience 23 (13): 5712-22.

Baloh, et al. Functional mapping of receptor specificity domains of glial cell line-derived neurotrophic factor (GDNF) family ligands and production of GFRalpha1 RET-specific agonists. J Biol Chem. Feb. 4, 2000;275(5):3412-20.

Barth et al. Boron neutron capture therapy of brain tumors: an emerging therapeutic modality. Neurosurgery. Mar. 1999;44(3):433-50; discussion 450-1.

Batzer, et al. Enhanced evolutionary PCR using oligonucleotides with inosine at the 3'-terminus. Nucleic Acid Res.1991;19:5081.

Beck, et al. 1994. Brain-Derived Neurotropic Factor Protects Against Ischemic Cell Damage in Rat Hippocampus. Journal of Cerebral Blood Flow and Metabolism 14: 689-92.

Begley et al., "Lysosomal storage diseases and the blood-brain barrier," Current Pharmaceutical Design, vol. 14, No. 16, pp. 1566-1580 (2008).

Bifare, et al. 2005. Brain-Derived Neurotropic Factor Protects against Multiple Forms of Brain Injury in Bacterial Meningitis. The Journal of Infectious Diseases 191: 40-45.

Boado et al., Genetic Engineering of IgG-glucuronidase fusion proteins, J. Drug Targeting 18(3):205-11 (2010).

(56) References Cited

OTHER PUBLICATIONS

Boado et al., "Genetic engineering of a lysosomal enzyme fusion protein for targeted delivery across the human blood-brain barrier," Biotechnology and Bioengineering, vol. 99, No. 2, pp. 475-484 (2008).

Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).

Boado et al., "Pharmacokinetics and brain uptake if a genetically engineered bifunctional fusion antibody targeting the mouse transferrin receptor," Molecular Pharmaceutics, vol. 7, No. 1, pp. 237-244 (2010).

Boado, et al. AGT-181: expression in CHO cells and pharmacokinetics, safety, and plasma iduronidase enzyme activity in Rhesus monkeys. Oct. 2009; 144(2):135-41.

Boado, et al. CHO cell expression, long-term stability, and primate pharmacokinetics and brain uptake of an IgG-paroxonase-1 fusion protein. Biotechnol Bioeng. Jan. 2011;108(1):186-96.

Boado, et al. Drug delivery of antisense molecules to the brain for treatment of Alzheimer's disease and cerebral AIDS. J Pharm Sci. Nov. 1998;87(11):1308-15.

Boado, et al. Engineering and expression of a chimeric trans ferrin receptor monoclonal antibody for blood-brain barrier delivery in the mouse. Biotechnol Bioeng. Mar. 1, 2009;102(4):1251-8.

Boado, et al. Fusion Antibody for Alzheimer's Disease with Bi-Directional Transport Across the Blood-Brain Barrier and Abeta Fibril Disaggregation. Bioconjug Chem. 2007;18(2):447-55.

Boado, et al. GDNF fusion protein for targeted-drug delivery across the human blood-brain barrier. Biotechnol Bioeng. Jun. 1, 2008;100(2):387-96.

Boado, et al. Genetic engineering, expression, and activity of a fusion protein of a human neurotrophin and a molecular Trojan horse for delivery across the human blood-brain barrier. Biotechnology and Bioengineering. 2007;97:1376-1386.

Boado, et al. Humanization of anti-human insulin receptor antibody for drug targeting across the human blood-brain barrier. Biotechnology and Bioengineering. 2007;96:381-391.

Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.

Boado, et al. Selective targeting of a TNFR decoy receptor pharmaceutical to the primate brain as a receptor-specific IgG fusion protein. J Biotechnol. Mar. 2010;146(1-2):84-91.

Brines, et al. Erythropoetin crosses the blood-brain barrier to protect against experimental brain injury, Proc Natl Acad Sci USA. 2000; 97:10526-10531.

Brummell, et al. Probing the combining site of an anti-carbohydrate antibody by saturation-mutagenesis: role of the heavy-chain CDR3 residues. Biochemistry. 1993; 32(4):1180-7.

Buchli, et al. Inhibition of Nogo: a key strategy to increase regeneration, plasticity and functional recovery of the lesioned central nervous system. Ann Med. 2005;37(8):556-67.

Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Carnicella, et al. GDNF is a fast-acting potent inhibitor of alcohol consumption and relapse. Proc Natl Acad Sci U S A. Jun. 10, 2008;105(23):8114-9.

Casset, et al. A peptide mimetic of an anti-CD4 monoclonal antibody by rational design. Biochem Biophys Res Commun. Jul. 18, 2003;307(1):198-205.

Cassol, et al. Stability of dried blood spot specimens for detection of human immunodeficiency virus DNA by polymerase chain reaction. J Clin Microbiol. Dec. 1992;30(12):3039-42.

Chen, et al. In vitro scanning saturation mutagenesis of all the specificity determining residues in an antibody binding site. Protein Engineering. 1999; vol. 12, No. 4, 349-56.

Cheng, et al. 1997. Marked Age-dependent Neuroprotection by Brain-derived Neurotropic Factor Against Neonatal Hypoxic-Ischemic Brain Injury. Annals of Neurology 41 (4): 521-29.

Cheng, et al. 2004. Neuroprotection for Ischemic Stroke: Two Decades of Success and Failure. The Journal of the American Society for Experimental Neuro Therapeutics 1: 36-45.

Chothia, et al. Canonical structures for the hypervariable regions of immunoglobulins. J Mol Biol. Aug. 20, 1987;196(4):901-17.

Chung et al. Antibodies against West Nile Virus nonstructural protein NS1 prevent lethal infection through Fc gamma receptor-dependent and -independent mechanisms. J Virol. Feb. 2006;80(3):1340-51.

Colman, P.M. Effects of amino acid sequence changes on antibody-antigen interactions. Res Immunol. Jan. 1994:145(1):33-6.

Coloma, et al. 1997. Design and production of novel tetravalent bispecific antibodies. Nat Biotechnol Feb;15(2):159-63.

Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.

Coloma, et al. The hinge as a spacer contributes to covalent assembly and is required for function of IgG. J Immnol. Jan. 15, 1997;158(2):733-40.

Cowen, et al. 2004. Neuropeptides: implications for alcoholism. Journal of Neurochemistry 89: 273-85.

Crow, et al. Biochemical and histopathological studies on patients with mucopolysaccharidoses, two of whom had been treated by fibroblast transplantation. J Clin Pathol. 1983 :36(4):415-30.

Dawson, et al. A comparative assessment of the efficacy and side-effect liability of the neuroprotective compounds in experimental stroke. 2001. Brain Research 892: 344-50.

De Pascalis, et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.

Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.

Deane, et al. IgG-assisted age-dependent clearance of Alzheimer's amyloid beta peptide by the blood-brain barrier neonatal Fc receptor. J Neurosci. 2005; 25(50):11495-503.

Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.

Dreier, et al. Recombinant immunocytokines targeting the mouse transferrin receptor: construction and biological activities. Bioconjug Chem. Jul.-Aug. 1998;9(4):482-9.

Duchnowska, et al. Central nervous system metastases in breast cancer patients administered trastuzumab. Cancer Treat Rev. Jun. 2005;31(4):312-8.

Duffy, et al. 1987. Blood-brain barrier transcytosis of insulin in developing rabbits. Brain Research 420: 32-38.

Duffy, et al. 1988. Human blood-brain barrier insulin-like growth factor receptor. Metabolism. Feb;37(2):136-40.

Durrington, et al. Paraoxonase and atherosclerosis. Arterioscler Thromb Vase Biol. Apr. 2001;21(4):473-80.

Ehrenreich, et al. Erythropoetin therapy for acute stroke is both safe and beneficial. Mol Med. Aug. 2002;8(8):495-505.

Eketjall, et al. Distinct structural elements in GDNF mediate binding to GFRalpha1 and activation of the GFRalpha1 -c-Ret receptor complex. EMBO J. Nov. 1, 1999;18(21:5901-10.

Elliott, et al. Control of rHuEPO biological activity: the role of carbohydrate. Exp Hematol. Dec. 2004;32(12):1146-55.

EP App. No. 07841110.5 Search Report and opinion dated Dec. 2, 2010.

EP Appl. No. 06825389.7 Search Report dated Feb. 23, 2010.

EP Appl. No. 08796594.3 Search Report and opinion dated Mar. 16, 2012.

EP10822810.7 Search Report dated Mar. 1, 2013.

Eslamboli, et al. Continuous Low-Level Glial Cell Line-Derived Neurotrophic Factor Delivery Using Recombinant Adeno-Associ-

(56) References Cited

OTHER PUBLICATIONS ated Viral Vectors Provides Neuroprotection and Induces Behavioral Recovery in a Primate Model of Parkinson's Disease. J. Neurosci. 2005 :25:769-77.
Ferber, D. Bridging the blood-brain barrier: new methods improve the odds of getting drugs to the brain cells that need them. PLoS Biol. Jun. 2007;5(6):e1 69: 1191-1194.
Fillebeen, et al. Receptor-mediated transcytosis of lactoferrin through the blood-brain barrier. J Biol Chem. Mar. 12, 1999;274(11):7011-17.
Forough, et al. Differential transforming abilities of non-secreted and secreted forms of human fibroblast growth factor-1. J Biol Chem. Feb. 5, 1993;268(4):2960-8.
Frenkel, et al. Modulation of Alzheimer's beta-amyloid neurotoxicity by site-directed single-chain antibody. J Neuroimmunol. Jul. 1, 2000;106(1-2):23-31.
Friden, et al. Blood-brain barrier penetration and in vivo activity of an NGF conjugate. Science. Jan. 15, 1993;259(5093):373-77.
Fu, et al. Neuroprotection in stroke in the mouse with intravenous erythropoietin-Trojan horse fusion protein. Brain Res. Jan. 19, 2011;1369:203-7. Epub Oct. 31, 2010.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Gennaro, 2000. Remington: The Science and Practice of Pharmacy. 20 ed.
Gillies, et al. Bi-functional cytokine fusion proteins for gene therapy and antibody-targeted tratment of cancer. 2002, Cancer Immunology and Immunotherapy, vol. 51, pp. 449-460.
Golden, et al. Human blood-brain barrier leptin receptor. Binding and endocytosis in isolated human brain microvessels. J Clin Invest. Jan. 1, 1997;99(1):14-8.
Grasso, et al. Neuroprotection by erythropoietin administration after experimental traumatic brain injury. Brain Res. Nov. 28, 2007;1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003;18(7):2093-8.
Habgood, et al. Changes in blood-brain barrier permeability to large and small molecules following traumatic brain injury in mice. Eur J Neurosci. Jan. 2007;25(1):231-8.
Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.
Hansson et al. Prediction of Alzheimer's disease using the CSF Abeta42/Abeta40 ratio in patients with mild cognitive impairment. Dement Geriatr Cogn Disord. 2007;23(5):316-20.
He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.
He, et al. Glial cell line-derived neurotrophic factor mediates the desirable actions of the anti-addiction drug ibogaine against alcohol consumption. J Neurosci. Jan. 19, 2005;25(3):619-28.
He, et al. Identification and characterization of the molecular lesion causing mucopolysaccharidosis type I in cats. Mol Genet Metab. 1999; 67(2):106-12.
Henikoff, et al. Amino acid substitution matrices from protein blocks. Proc Natl Acad Sci U S A. 1992; 89(22):10915-9.
Henikoff, et al. Predicting the effects of amino Acid substitutions on protein function. Annu Rev Genomics Hum Genet. 2006;7:61-80.
Iietman, et al. Neuroprotection by Brain-derived Neurotropic Factor Is Mediated by Extracellular Signal-regulated Kinase and Phoshatidylinositol 3-Kinase. The J of Bio Chem. 1999. 274 (32): 22569-80.
Holliger, et al. Engineered antibody fragments and the rise of single domains. Nat Biotechnol. Sep. 2005 ;23(9):1126-36.
Hoshaw, et al. Central administration of IGF-I and BDNF leads to long-lasting antidepressant-like effects. Brain Res. 2005. 1037: 204-8.
Huston, et al. Protein engineering of antibody binding sites: recovery of specific activity in an anti-digoxin single-chain Fv analogue produced in *Escherichia coli* Proc Natl Acad Sci U S A. 1988; 85(16):5879-83.
Ibanez, et al. An extended surface of binding to Trk tyrosine kinase receptors in NGF and BDNF allows the engineering of a multifunctional pan-neurotrophin. EMBO J. Jun. 1993;12(6):2281-93.
Ibanez, Structure-function relationships in the neurotrophin family. J Neurobiol. Nov. 1994;25(11):1349-61.
Iwasaki, et al. Protective effect of interleukin-3 and erythropoietin on motor neuron death after neonatal axotomy. Neurol Res. Oct. 2002;24(7):643-6.
Jefferies, et al. Analysis of lymphopoietic stem cells with a monoclonal antibody to the rat transferrin receptor. Immunology. Feb. 1985;54(2):333-41.
Jethwa, et al. 2004. Neuromedin U has a physiological role in the regulation of food intake and partially mediates the effects of leptin. American Journal of Physiology-Endocrinology and Metabolism 289: E301-E305.
Jiang, et al. BDNF Variation and Mood Disorders: A Novel Functional Promoter Polymorphism and Val66Met are Associated with Anxiety but Have Opposing Effects. 2005. Neuropsychopharmacology 30:1353-61.
Josse, et al. Identification of residues essential for human paraoxonase (PON1) arylesterase/organophosphatase activities. Biochemistry. Mar. 2, 1999 ;38(9):2816-25.
Josse, et al. Oligomeric states of the detergent-solubilized human serum paraoxonase (PON1). J Biol. Chem. Sep. 6, 2002;277(36):33386-97.
Josse, et al. The active site of human paraoxonase (PON1). J Appl Toxicol. Dec. 2001;21 Supp 1 1:S7-11.
Juul, et al. Erythropoietin concentrations in cerebrospinal fluid of nonhuman primates and fetal sheep following high-dose recombinant erythropoietin, Biol. Neonate. 2004;85:138-144.
Kabat, et al., Sequences of Proteins of Immunological Interest. 5th Ed. Public Health Service, National institutes of Health, Bethesda, MD. 1991;pp. 647-649.
Kakkis, et al. Overexpression of the human lysosomal enzyme alpha-L-iduronidase in Chinese hamster ovary cells. Protein Expr Purif 1994; 5(3):225-32.
Karlin, et al. Applications and statistics for multiple high- scoring segments in molecular sequences. Proc. Natl. Acad. Sci. USA. 1993;90:5873-87.
Kashmiri, et al. SDR grafting—a new approach to antibody humanization. Methods. May 2005;36(1):25-34.
Kastin, et al. Glial cell line-derived neurotrophic factor does not enter normal mouse brain. Neuroscience Letters. 2003;340:239-41.
Kido, et al. 2000. Neuroprotective effects of brain-derived neurotropic factor in eyes with NMDA-induced neuronal death. Brain Research 884:59-67.
Kim, et al. Decreased paraoxonase-1 activity is a risk factor for ischemic stroke in Koreans. Biochem Biophys Res Commun. Dec. 7, 2007;364(1):157-62.
Kim, et al., Continuous Brain-derived Neurotropic Factor (BDNF) Infusion After Methylprednisolone Treatment in Severe Spinal Cord Injury. Journal of Korean Medical Science 2003;19: 113-22.
Kitagawa, et al. Reduction of Ischemic Brain Injury by Topical Application of Glial Cell Line—Derived Neurotrophic Factor After Permanent Middle Cerebral Artery Occlusion in Rats. Stroke. 1998;29:1417-22.
Knaust, "Residues Critical for Formylglycine Formation and/or Catalytic Activity of Arylsulfatase A," American Chemical Society, 37:13941-13946 (1998).
Kobayashi, et al. Intracerebral Infusion of Glial Cell Line-Derived Neurotrophic Factor Promotes Striatal Neurogenesis After Stroke in Adult Rats Stroke. 2006;37:2361-67.

(56) References Cited

OTHER PUBLICATIONS

Koehne, et al. Vascular endothelial growth factor and erythropoietin concentrations in cerebrospinal fluid of children with hydrocephalus. Childs Nerv Syst. Apr. 2002;18(3-4):137-41.

Krewson, et al. Distribution of nerve growth factor following direct delivery to brain interstitium. Brain Research 680: 196-206 (1995).

Kurihara, et al. Imaging Brain Tumors by Targeting Peptide Radiopharmaceuticals through the Blood-Brain Barrier. Cancer Research 59: 6159-63 (1999).

Lai, et al. Structural determinants of Trk receptor specificities using BDNF-based neurotrophin chimeras. J Neurosci Res. Dec. 1, 1996;46(5):618-29.

Lang, et al. Randomized controlled trial of intraputamenal glial cell line-derived neurotrophic factor infusion in Parkinson disease. Annals of Neurology. 2006;59:459-66.

Lapchak, et al. Glial cell line-derived neurotrophic factor attenuates behavioural deficits and regulates nigrostriatal dopaminergic and peptidergic markers in 6- hydroxydopamine-lesioned adult rats: comparison of intraventricular and intranigral delivery. Neuroscience. 1997;78:61-72.

Lazar, et al. Transforming growth factor alpha: mutation of aspartic acid 47 and leucine 48 results in different biological activities. Mol Cell Biol. Mar. 1988;8(3):1247-52.

Lee, et al. Drug targeting to the brain using avidin-biotin technology in the mouse; (blood-brain barrier, monoclonal antibody, transferrin receptor, Alzheimer's disease). J Drug Target. 2000;8(6):413-24.

Lee, et al., Imaging Brain Amyloid of Alzheimer Disease in Vivo in Transgenic Mice With an Aβ Peptide Radiopharmaceutical. Journal of Cerebral Blood Flow and Metabolism 2002;22: 223-31.

Lenz, et al. Stoichiometric and catalytic scavengers as protection against nerve agent toxicity: a mini review. Toxicology. Apr. 20, 2007;233(1-3):31-9.

Lewin, B. Genes IV. Oxford University Press. 1990. p. 810.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Lin, et al. GDNF: a glial cell line-derived neurotrophic factor for midbrain dopaminergic neurons. Science. 1993;260:1130-32.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Liu, et al. Anti beta-amyloid (Abeta) SCFV inhibits Abeta aggregation and neurotoxicity (P4-354). Neurobiology of Aging, Tarrytown, NY. 2004;25:S575-S576.

Liu, et al. Single chain variable fragments against beta-amyloid (Abeta) can inhibit Abeta aggregation and prevent abeta-induced neurotoxicity. Biochemistry. Jun. 8, 2004;43(22):6959-67.

Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).

Lu et al., "Genetic Engineering of a Bifunctional IgG fusion protein with iduronate-2-sulfatase," Bioconjugate Chemistry, 21(1) pp. 151-156 (2010).

Lu, et al. Cationic Liposome-Mediated GDNF Gene Transfer after Spinal Cord Injury. Journal of Neurotrauma. 2002;19:1081-1090.

Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

Maccallum, et al. Antibody-antigen interactions: contact analysis and binding site topography. J Mol Biol. Oct. 11, 1996;262(5):732-45.

Manoutcharian, et al. Amyloid-beta peptide-specific single chain Fv antibodies isolated from an immune phage display library. J Neuroimmunol. 2003; 145(1-2):12-7.

Martell, et al. Efficacy of transferrin receptor-targeted immunotoxins in brain tumor cell lines and pediatric brain tumors. Cancer Res. Mar. 15, 1993 ;53(6):1348-53.

Martin et al. Crystal structure at 2.8 A of an FcRn/heterodimeric Fc complex: mechanism of pH-dependent binding. Mol Cell. Apr. 2001;7(4):867-77.

Marvin, et al. Recombinant approaches to IgG-like bispecific antibodies. Acta Pharmacol Sin. Jun. 2005;26(6):649-58.

Matis, et al. Erythropoietin in spinal cord injury. Eur Spine J. Mar. 2009;18(3):314-23.

McGrath, et al. Bifunctional fusion between nerve growth factor and a transferrin receptor antibody. J Neurosci Res. Jan. 15, 1997;47(2):123-33.

McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.

Menzies, et al. Contributions of ions and albumin to the formations and resolution of ischemic brain edema. Journal of Neurosurgery 78: 257-266. (1993).

Messer, et al. Role for GDNF in biochemical and behavioral adaptations to drugs of abuse. Neuron. Apr. 2000;26(1):247-57.

Mori, et al. Differential expression patterns of TrkB ligands in the macaque monkey brain. Developmental Neuroscience 15: 2507-11 (2004).

NCBI GenBank Accession No. NM-000487 (Oct. 23, 2011).

Needleman, et al. A general method applicable to the search for similarities in the amino acid sequence of two proteins. J. Mol. Biol. 1970;48:443-53.

Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.

Ng, et al. Predicting the effects of amino acid substitutions on protein function. Annual Review of Genomics and Human Genetics. 2006;7:61-80.

Notice of Allowance dated Aug. 9, 2011 for U.S. Appl. No. 11/245,710.

Notice of Allowance dated Oct. 28, 2011 for U.S. Appl. No. 12/688,842.

Notice of Allowance dated Oct. 31, 2011 for U.S. Appl. No. 11/245,546.

Nutt, et al., Randomized, double-blind trial of glial cell line-derived neurotropic factor (GDNF) in PD. Neurology 2003;60: 69-73.

Ober, et al. Differences in promiscuity for antibody-FcRn interactions across species: implications for therapeutic antibodies. Int Immunol. Dec. 2001;13(1 2):1551-9.

Ohtsuka, et al. An alternative approach to deoxyoligonucleotides as hybridization probes by insertion of Deoxyinosine at Ambiguous Codon Positions. J. Biol. Chem. 1985;260:2605-08.

Osbourn, et al. Directed selection of MIP-1 alpha neutralizing CCR5 antibodies from a phage display human antibody library. Nat Biotechnol. Aug. 1998;16(8):778-81.

Padlan, et al. Identification of specificity-determining residues in antibodies. FASEB J. 1995; 9(1):133-9.

Padlan, et al. Structure of an antibody-antigen complex: crystal structure of the HyHEL-10 Fab-lysozyme complex. Proc Natl Acad Sci U S A. Aug. 1989;86(1 5):5938-42.

Paragh, et al. Ciprofibrate increases paraoxonase activity in patients with metabolic syndrome. Br J Clin Pharmacol. Jun. 2006;61(6):694-701.

Pardridge, The Blood-Brain Barrier: Bottleneck in Brain Drug Development. NeuroRx: The Journal of the American Society for Experimental NeuroTherapeutics 2:3-14 (2005).

Pardridge, "Re-engineering biopharmaceuticals for delivery to brain with molecular Trojan horses," Bioconjugate Chemistry, vol. 18, No. 7, pp. 1327-1338 (2008).

Pardridge, Blood-Brain Barrier Drug Targeting: The Future of Brain Drug Development. Molecular Interventions 3: 90-105 (2003).

Pardridge, Brain drug targeting: The future of brain drug development. Cambridge University Press (2001).

Pardridge, Drug Targeting to the Brain. Pharm Res 24:1733-44 (2007).

(56) References Cited

OTHER PUBLICATIONS

Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).
Pardridge, et al. Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582 (1998).
Pardridge, et al. Drug and gene targeting to the brain with molecular Trojan horses. Nat Rev Drug Discov., Feb;1(2):131-9 (2002).
Pardridge, et al. Human Blood-Brain Barrier Transferrin Receptor. Metabolism 36: 892-95 (1987).
Pardridge, et al. Transport of histone through the blood-brain barrier. J Pharmacol Exp Ther. Dec;251(3):821-6. (1989).
Pardridge, et al. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46 (1993).
Pardridge, Neuroprotection in stroke: is it time to consider large-molecule drugs? Drug Discovery Today 6: 751-53 (2001).
Pardridge, Neurotrophins, neuroprotection and the blood-brain barrier. Current Opinion in Investigational Drugs 3 (12): 1753-57 (2002).
Pardridge, The Blood-Brain Barrier and Neurotherapeutics. NeuroRx: The Journal of the American Society for Experimental NeuroTherapeutics 2 (1): 1-2 (2005).
Park, et al. Production and characterization of fusion proteins containing transferrin and nerve growth factor. J Drug Target. 1998;6(1):53-64.
Patel, et al. Intraputamenal infusion of glial cell line-derived neurotrophic factor in PD: A two-year outcome study. Annals of Neurology. 2005;57:298-302.
Paul, W. Fundamental Immunology. 3rd Edition. 1993;292-95.
PCT Application No. US06/38587 ISR dated Jul. 1, 2008.
PCT Application No. US07/76316 ISR dated Sep. 16, 2008.
PCT Application No. US08/71121 ISR dated Feb. 27, 2009.
PCT Application No. US10/27882 ISR dated Sep. 7, 2010.
PCT Application No. US11/21418 ISR and Written Opinion dated Apr. 8, 2011.
PCT/US2012/054520 International Search Report dated Feb. 22, 2013.
Pearson, et al. Improved Tools for Biological Sequence Comparison. Proc. Nat'l Acad. Sci. USA. 1988;85:2444-48.
Pearson, Rapid and sensitive sequence comparison with FASTP and FASTA. Meth. Enzymol. 1990;183:63-98.
Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.
Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-26.
Pluckthun, A. Antibodies from *Escherichia coli*. In the Pharmacology of Monoclonal Antibodies. vol. 113, Rosenburg and Moore eds. Springer-Verlag, New York. 1994;pp. 269-315.
Polito et al., "IDS Crossing of the Blood-Brain Barrier Corrects CNS Detects in MPSII Mice," Amer. Journ. Human Genetics, vol. 85, No. 2, pp. 296-301 (2009).
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Preston, et al. 1997. Evidence for pore-like opening of the blood-brain barrier following forebrain is chemia in rats. Brain Research 761: 4-10.
Raghavan, et al. Analysis of the pH dependence of the neonatal Fc receptor/immunoglobulin G interaction using antibody and receptor variants. Biochemistry. Nov. 14, 1995;34(45):14649-57.
Ratliff-Schaub, et al. 2005. Randomized controlled trial of transdermal secretion on behavior of children with autism. Autism 9 (3): 256-65.
Reiber, et al. Protein transfer at the blood cerebrospinal fluid barrier and the quantitation of the humoral immune response within the central nervous system. Clin Chim Acta. Mar. 30, 1987;163(3):319-28.
Rempel, et al. A homology model for human α-L-Iduronidase: Insights into human disease. Mol. Genetics and Met. 2005; 85:28-37.
Robinson, et al. The structures of the neurotrophin 4 homodimer and the brain-derived neurotrophic factor / neurotrophin 4 heterodimer reveal a common Trk-binding site. Protein Science 1999 8: 2589-97.
Rochu, et al. Human paraoxonase: a promising approach for pre-treatment and therapy of organophosphorus poisoning. Toxicology. Apr. 20, 2007;233(1-3):47-59.
Rossolini, et al. Use of deoxyinosine-containing primers vs degenerate primers for polymerase chain reaction based on ambiguous sequence information. Mol. Cell. Probes. 1994;8(2):91-98.
Rudikoff, et al. Single amino acid substitution altering antigen-binding specificity. Proc Natl Acad Sci U S A. Mar. 1982;79(6):1979-83.
Ruiz-Leon, et al. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120;2003:1019-26.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.
Sampson et al. Unarmed, tumor-specific monoclonal antibody effectively treats brain tumors. Proc Nati Acad Sci U S A. Jun. 20, 2000;97(13):7503-8.
Sariola, et al. Novel functions and signalling pathways for GDNF. J Cell Sci. Oct. 1, 2003;116(Pt 19):3855-62.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Expression of the neonatal Fc receptor (F cRn) at the blood-brain barrier. J Neurochem. Apr. 2002;81(1):203-6.
Schlachetzki, et al. Gene therapy of the brain: the trans-vascular approach. Neurology. Apr. 27, 2004;62(8):1275-81.
Schwartz, et al. A superactive insulin: [B10-aspartic acid] insulin (human). Proc Natl Acad Sci U S A. Sep. 1987;84(18):6408-11.
Scott, et al. Human alpha-L-iduronidase: cDNA isolation and expression. Proc Natl Acad Sci U S A. Nov. 1, 1991;88(21):9695-9.
Sellers, On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Shanafelt, et al. Identification of critical amino acid residues in human and mouse granulocyte-macrophage colony-stimulating factor and their involvement in species specificity. J Biol. Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.
Sifuentes, et al. A follow-up study of MPS I patients treated with laronidase enzyme replacement therapy for 6 years. Mo1 Genet Metab. Feb. 2007;90(2):171-80. Epub Sep. 29, 2006.
Siren, et al., Erythropoetin prevents neuronal apoptosis after cerebral ischemi a and metabolic stress. Proc Natl Acad Sci U S A. Mar. 27, 2001;98(7):4044-9.
Skolnick, et al. From genes to protein structure and function: novel applications of computational approaches in the genomic era. Trends Biotechnol. Jan. 2000;18(1):34-9. Review.
Smith, et al. Comparison of Biosequences. Adv. Appl. Math. 1981 1;482-89.
Soukharev, et al. A fluorogenic substrate for detection of organophosphatase activity. Anal Biochem. Apr. 2004;327(1):140-8.

(56) References Cited

OTHER PUBLICATIONS

Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry 1992;59 (1): 99-106.
Strauss, et al., Brain-derived neurotrophic factor variants are associated with childhood-onset mood disorder: confirmation in a Hungarian sample. Molecular Psychiartry 2005;10: 861-67.
Takahashi, et al., Inhibition of cell growth and tumorigenesis of human glioblastoma cells by a neutralizing antibody against human basic fibroblast growth factor. Federation of European Biochemical Societies 1991;288 (1,2): 65-71.
The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.
Tougou, et al. Paraoxonase has a major role in the hydrolysis of prulifloxacin (NM441), a prodrug of a new antibacterial agent. Drug Metab Dispos. Apr. 1998;26(4):355-9.
Triguero et al. Capillary depletion method for quantification of blood-brain barrier transport of circulating peptides and plasma proteins. J Neurochem. 1990; 54(6):1882-8.
Tsukahara, et al. The Role of Brain-derived Neurotrophic Factor in Transient Forebrain Ischemia in the Rat Brain. Neurosurgery 34 (2);1994:323-31.
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Unger, et al. Recombinant α-iduronidase: characterization of the purified enzyme and correction of mucopolysaccharidosis type I fibroblasts. Biochem J. 1994; 384:43-49.
U.S. Appl. No. 10/307,165 Office Action dated Feb. 10, 2006.
U.S. Appl. No. 10/307,165 Office Action dated Mar. 1, 2007.
U.S. Appl. No. 10/307,165 Office Action dated Aug. 17, 2007.
U.S. Appl. No. 10/307,165 Office Action dated Aug. 18, 2006.
U.S. Appl. No. 10/307,276 Office Action dated Feb. 22, 2006.
U.S. Appl. No. 10/307,276 Office Action dated Apr. 9, 2007.
U.S. Appl. No. 10/307,276 Office Action dated Jul. 19, 2006.
U.S. Appl. No. 10/307,276 Office Action dated Oct. 29, 2007.
U.S. Appl. No. 11/061,956 Office Action dated May 9, 2008.
U.S. Appl. No. 11/061,956 Office Action dated May 23, 2006.
U.S. Appl. No. 11/061,956 Office Action dated Nov. 13, 2007.
U.S. Appl. No. 11/061,956 Office Action dated Dec. 21, 2006.
U.S. Appl. No. 11/245,546 Office Action dated Jan. 23, 2009.
U.S. Appl. No. 11/245,546 Office Action dated Jun. 27, 2011.
U.S. Appl. No. 11/245,546 Office Action dated Jul. 1, 2010.
U.S. Appl. No. 11/245,546 Office Action dated Jul. 2, 2008.
U.S. Appl. No. 11/245,546 Office action dated Oct. 18, 2011.
U.S. Appl. No. 11/245,546 Office Action dated Oct. 20, 2009.
U.S. Appl. No. 11/245,546 Office Action dated Nov. 8, 2007.
U.S. Appl. No. 11/245,710 Office Action dated Jan. 15, 2008.
U.S. Appl. No. 11/245,710 Office Action dated Feb. 2, 2010.
U.S. Appl. No. 11/245,710 Office Action dated Apr. 6, 2011.
U.S. Appl. No. 11/245,710 Office Action dated Apr. 13, 2007.
U.S. Appl. No. 11/245,710 Office Action dated Jun. 3, 2008.
U.S. Appl. No. 11/245,710 Office Action dated Jul. 2, 2009.
U.S. Appl. No. 11/245,710 Office Action dated Sep. 20, 2007.
U.S. Appl. No. 11/245,710 Office Action dated Oct. 12, 2010.
U.S. Appl. No. 11/245,710 Office Action dated Oct. 15, 2007.
U.S. Appl. No. 11/245,710 Office Action dated Nov. 10, 2008.
U.S. Appl. No. 11/245,710 Office Action dated Nov. 13, 2006.
U.S. Appl. No. 11/841,541 Office Action dated Jun. 17, 2009.
U.S. Appl. No. 11/841,541 Office Action dated Dec. 16, 2009.
U.S. Appl. No. 11/841,594 Office Action dated Mar. 26, 2010.
U.S. Appl. No. 11/841,594 Office Action dated Oct. 30, 2009.
U.S. Appl. No. 11/841,623 Office Action dated Jan. 15, 2009.
U.S. Appl. No. 11/841,623 Office Action dated Sep. 24, 2009.
U.S. Appl. No. 11/893,281 Office Action dated Feb. 16, 2011.
U.S. Appl. No. 11/893,281 Office Action dated May 12, 2010.
U.S. Appl. No. 11/893,281 Office action dated Oct. 13, 2009.
U.S. Appl. No. 12/150,983 Office Action dated Feb. 16, 2011.
U.S. Appl. No. 12/150,983 Office Action dated Sep. 15, 2010.
U.S. Appl. No. 12/179,806 Office Action dated Mar. 10, 2010.
U.S. Appl. No. 12/179,806 Office Action dated Jul. 31, 2009.
U.S. Appl. No. 12/323,232 Office Action dated Mar. 26, 2010.
U.S. Appl. No. 12/323,232 Office Action dated Aug. 20, 2009.
U.S. Appl. No. 12/558,348 Office Action dated Mar. 7, 2011.
U.S. Appl. No. 12/574,571 Office Action dated Mar. 18, 2011.
U.S. Appl. No. 12/574,571 Office Action dated Dec. 14, 2011.
U.S. Appl. No. 12/688,842 Office Action dated May 13, 2011.
U.S. Appl. No. 12/756,093 Office Action dated Jul. 20, 2012.
US Notice of Allowance—U.S. Appl. No. 11/245,546 dated Apr. 1, 2011.
Wang, et al. Identification of the key amino acids of glial cell line-derived neurotrophic factor family receptor alpha1 involved in its biological function. J Biol Chem. Jan. 2, 2004;279(1):109-16.
Ward, E.S. Binding activities of a repertoire of single immunoglobulin variable domains secreted from *Escherichia coli*. Nature. Oct. 12, 1989;341(6242):484-5.
Warrington, et al. Human monoclonal antibodies reactive to oligodendrocytes promote remyelination in a model of multiple sclerosis. Proc Natl Acad Sci U S A. Jun. 6, 2000;97(12):6820-5.
Weich, et al. Interleukin-3/erythropoietin fusion proteins: in vitro effects on hematopoietic cells. Exp Hematol. May 1993;21(5):647-55.
Whetstone, et al. Blood-spinal cord barrier after spinal cord injury: relation to revascularization and wound healing. J Neurosci Res. Oct. 15, 2003;74(2):227-39.
Whittaker, et al. Characterization of the functional insulin binding epitopes of the full-length insulin receptor. J Biol Chem. 2005;280(22):20932-6.
Wiesenhofer, et al. Glial cell line-derived neurotrophic factor (GDNF) and its receptor (GFR-α1) are strongly expressed in human gliomas. Acta Neuropathol. (Berl). 2000;99:131-37.
Wraith, J. Enzyme replacement therapy in mucopolysaccharidosis type I: progress and emerging difficulties. J Inherit Metab Dis. Apr. 2001;24(2):245-50.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection with noninvasive neurotrophin delivery to the brain. Proc Natl Acad Sci U S A. Jan. 5, 1999;96(1):254-9.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12 (4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.
Yan, et al. 2007 Enduring vulnerability to reinstatement of methamphetamine-seeking behavior in glial-cell-line-derived neurotrophic factor mutant mice. FASEB J. Jul;21(9):1994-2004.
Yip, et al. Three-dimensional structural interactions of insulin and its receptor. J Biol Chem. Jul. 25, 2003;278(30):27329-32.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Mediated efflux of IgG molecules from brain to blood across the blood-brain barrier. J Neuroimmunol. Mar. 1; 114(1-2):168-72.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2001. Rapid transferrin efflux from brain to blood across the blood-brain barrier. J Neurochem. Mar;76(5):1597-600.
Zhang, et al. 2003. Global Non-Viral Gene Transfer to the Primate Brain Following Intravenous Administration. Molecular Therapy 7 (1): 11-18.
Zhang, et al. Mediated efflux of IgG molecules from brain to blood across the blood-brain barrier. J Neuroimmunol. Mar. 1, 2001;114(1-2):168-72.

(56) References Cited

OTHER PUBLICATIONS

Zhou, et al. Brain penetrating IgG-erythropoietin fussion protein is neuroprotective following intravenous treatment in Parkinson's disease in the mouse. Brain Res. Mar. 25, 2011;1382:315-20. Epub Jan. 26, 2011.
Aronovich et al., "Molecular Genetic Defect Underlying α-L-Iduronidase," Am. Journ. Hum. Genet. 58: 75-85 (1996).
Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme.2009.10.002. Epub Oct. 13, 2009.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Degraaf, M. et al., "Expression of scFvs and scFv Fusion Proteins in Eukaryotic Cells." Methods in Biology, 2001, vol. 178: Antibody Phage Display: Methods and Protocols, p. 379-387.
EP10754139 Search Report dated Dec. 13, 2012.
Flomen, et al. Determination of the organisation of coding sequences within the iduronate sulphate sulphatase (IDS)gene. Hum. Mol. Genet. 1993;2(1):5-10.
Franco, et al. A cluster of sulfatase genes on Xp22.3: mutations in chondrodysplasia punctata (CDPX) and implications for warfarin embryopathy. Cell. Apr. 7, 1995;81(1):15-25.
Hui et al., "Tumor Necrosis Factor Receptor-IgG Fusion Protein for Targeted Drug Delivery across the Human Blood-Brain Barrier," vol. 6, No. 5, pp. 1536-1543 (2009).
Muenzer, et al. A phase II/III clinical study of enzyme replacement therapy with idursulfase in mucopolysaccharidosis II (Hunter syndrome). Genet Med Aug. 2006;8(8):465-73.
Muenzer, et al. Advances in the treatment of mucopolysaccharidosis type I. N. Engl J Med. May 6, 2004;350(19):1932-4.
Nawashiro et al., "Neuroprotective effects of TNF binding protein in focal cerebral ischemia," Brain Research, vol. 778, No. 2, pp. 265-271 (1997).
NCBI Reference Sequence: NM-000202.5 *Homo sapiens* iduronate 2-sulfatase (IDS), transcript variant 1, mRNA. 1992. http://www.ncbi.nlm.nih.gov/nuccore/NM000202.5.
Pardridge et al., "Biologic TNF[alpha]-inhibitors that cross the human blood-brain barrier," Bioengineered Bugs, Landes Bioscience, vol. 1, No. 4, pp. 231-234 (2010).
Pardridge et al., "Blood-brain barrier delivery of protein and non-viral gene therapeutics with molecular Trojan horses," Journal of Controlled Release, vol. 122, No. 3, pp. 345-348 (2007).
Pardridge, Tyrosine Hydroxylase Replacement in Experimental Parkinson's Disease with Transvascular Gene Therapy. NueuoRx: Journal of the American Society for Experimental NeuroTherapeutics. 2(1):129-138. (2005).
Pardrige et al. "Re-engineering biopharmaceuticals for delivery to brain with molecular Trojan horses," Bioconjugate Chemistry, vol. 19, No. 7 (2008).
PCT Application No. US10/52113 ISR dated Feb. 22, 2011.
Schoonjans, R. et al., "Fab Chains As an Efficient Heterodimerization Scaffold for the Production of Recombinant Bispecific and Trispecific Antibody Derivatives." The Journal of Immunology, 2000, 165 (12): 7050-7057.
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
Tobinick et al., "Perispinal etanercept for neuroinflammatory disorders," Drug Discovery Today, vol. 14, No. 3-4, pp. 168-177 (2009).
Tomatsu, et al. Murine model (Galns( tm(C76S)slu)) of MPS IVA with missense mutation at the active site cystein conserved among sulfatase proteins. Mol Genet Metab. Jul. 2007;91(3):261-8.
U.S. Appl. No. 12/179,806 Office Action dated Apr. 24, 2013.
U.S. Appl. No. 12/901,481 Office Action dated Jan. 9, 2013.
U.S. Appl. No. 11/841,541 Office Action dated Mar. 26, 2013.
U.S. Appl. No. 11/841,594 Notice of Allowance dated Apr. 2, 2013.
U.S. Appl. No. 13/609,099 Notice of Allowance dated Mar. 20, 2013.
U.S. Appl. No. 13/609,099 Office Action dated Nov. 26, 2012.
Voznyi, et al. A fluorimeteric enzyme assay for the diagnosis of MPS II (Hunter disease). J Inherit Metab Dis. 2001;24:675-80.
Wraith, et al. Mucopolysaccaridosis type II (Hunter syndrome): a clinical review and recommendations for treatment in the era of enzyme replacement therapy. Eur J Pediatr. Mar. 2008;167(3):267-77.
Wu, et al. Neuroprotection in Experimental Stroke with Targeted Neurotrophins. NeuroRX: The Journal of the American Society for Experimental NeuroTherapeutics. 2005;2(1):120-128.
Zito, et al. Sulphatase activities are regulated by the interaction of sulphatase-modifying factor 1 with SUMF2, EMBO Rep 2005;6(7):655-660.
Albeck, et al. A non-invasive transport system for GDNF across the blood-brain barrier. NeuroReport. Jul. 7, 1997; 8(9-10):2293-2298.
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010.
Board of Patent Appeals and Interferences (BPAI) Decision dated Jul. 22, 2010 from U.S. Appl. No. 11/061,956.
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
European search report dated Jul. 15, 2013 for EP Application No. 11733492.
Gehrmann, et al. Biochemical properties of recombinant human beta-glucuronidase synthesized in baby hamster kidney cells. Biochem J. Aug. 1, 1994;301 (Pt 3):821-8.
Jeffrey, et al. 26-10 Fab-digoxin complex. Affinity and specificity due to surface complementarity. Proc Natl. Acad. Sci USA. 1993; 90(21):10310-10314.
Notice of allowance dated Sep. 23, 2013 for U.S. Appl. No. 12/756,093.
Notice of allowance dated Oct. 7, 2013 for U.S. Appl. No. 12/323,232.
Office action dated Oct. 22, 2013 for U.S. Appl. No. 12/901,481.
Office action dated Nov. 4, 2013 for U.S. Appl. No. 12/179,806.
Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Schuchman, et al. Human alpha-L-iduronidase: Purification and properties of the high uptake (higher molecular weight) and the low uptake (processed) forms. J. Bioi. Chem. 1984; 259(5):3132-3140.
Shipley, et al. The role of glycosylation and phosphorylation in the expression of active human beta-glucuronidase. J Biol Chem. Jun. 5, 1993;268(16):12193-8.
Thompson, et al. Improved binding of a bivalent single-chain immunotoxin results in increased efficacy for in vivo T-cell depletion. Protein Eng. Dec. 2001;14(12):1035-41.
Wu, et al. Simultaneous targeting of multiple disease mediators by a dual-variable-domain immunoglobulin. Nat Biotechnol. Nov. 2007;25(11):1290-7. Epub Oct. 14, 2007.
U.S. Appl. No. 14/144,460, filed Dec. 30, 2013, Pardridge et al.
Benito, et al. Beta-galactosidase enzymatic activity as a molecular probe to detect specific antibodies. J Biol Chem. Aug. 30, 1996;271(35):21251-6.
Corchero, et al. The position of the heterologous domain can influence the solubility and proteolysis of beta-galactosidase fusion proteins in *E. coli*. J Biotechnol. Jul. 31, 1996;48(3):191-200.
Notice of allowance dated Jan. 22, 2014 for U.S. Appl. No. 12/323,232.
Notice of allowance dated Dec. 23, 2013 for U.S. Appl. No. 11/841,541.
Notice of allowance dated Dec. 16, 2013 for U.S. Appl. No. 12/756,093.

* cited by examiner

Figure 5

HIR Ab HC (SEQ ID NO:7)

MDWTWRVFCLLAVAPGAHSQVQLQQSGPELVKPGALVKISCKASGYTFTNYDIHWVKQRP
GQGLEWIGWIYPGDGSTKYNEKFKGKATLTADKSSSTAYMHLSSLTSEKSAVYFCAREWA
YWGQGTLVTVSAASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGS

Figure 6

HIR Ab LC (SEQ ID NO:8)

METPAQLLFLLLLWLPDTTGDIQMTQSPSSLSASLGERVSLTCRASQDIGGNLYWLQQGP
DGTIKRLIYATSSLDSGVPKRFSGSRSGSDYSLTISSLESEDFVDYYCLQYSSSPWTFGG
GTKMEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

Figure 7

| HIR Ab HC CDRs | | |
|---|---|---|
| CDR1 | GYTFTNYDIH | SEQ ID NO:1 |
| CDR2 | WIYPGDGSTKYNEKFKG | SEQ ID NO:2 |
| CDR3 | EWAY | SEQ ID NO:3 |
| HIR Ab LC CDRs | | |
| CDR1 | RASQDIGGNLY | SEQ ID NO:4 |
| CDR2 | ATSSLDS | SEQ ID NO:5 |
| CDR3 | LQYSSSPWT | SEQ ID NO:6 |

Figure 8

Amino Acid Sequence of ASA (minus signal peptide)
(SEQ ID NO:9)

```
RPPNIVLIFADDLGYGDLGCYGHPSSTTPNLDQLAAGGLRFTDFYVPVSLCTPSRAALLTGRLPV
RMGMYPGVLVPSSRGGLPLEEVTVAEVLAARGYLTGMAGKWHLGVGPEGAFLPPHQGFHRFLGIP
YSHDQGPCQNLTCFPPATPCDGGCDQGLVPIPLLANLSVEAQPPWLPGLEARYMAFAHDLMADAQ
RQDRPFFLYYASHHTHYPQFSGQSFAERSRGPFGDSLMELDAAVGTLMTAIGDLGLLEETLVIF
TADNGPETMRMSRGGCSGLLRCGKGTTYEGGVREPALAFWPGHIAPGVTHELASSLDLLPTLAAL
AGAPLPNVTLDGFDLSPLLLGTGKSPRQSLFFYPSYPDEVRGVFAVRSGKYKAHFFTQGSAHSDT
TADPACHASSSLTAHEPPLLYDLSKDPGENYNLLGGVAGATPEVLQALKQLQLLKAQLDAAVTFG
PSQVARGEDPALQICCHPGCTPRPACCHCPDPHA
```

Figure 9

Amino Acid Sequence of HIRMAb-HC-ASA (SEQ ID NO:10)

MDWTWRVFCLLAVAPGAHSQVQLQQSGPELVKPGALVKISCKASGYTFTNYDIHWVKQRPGQGLE
WIGWIYPGDGSTKYNEKFKGKATLTADKSSSTAYMHLSSLTSEKSAVYFCAREWAYWGQGTLVTV
SAASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGSSSRPPNIVLIFADDLGYGDLGCYGHPSSTTPNLDQLAAGGLRFTDFYVPVSLCTPSRA
ALLTGRLPVRMGMYPGVLVPSSRGGLPLEEVTVAEVLAARGYLTGMAGKWHLGVGPEGAFLPPHQ
GFHRFLGIPYSHDQGPCQNLTCFPPATPCDGGCDQGLVPIPLLANLSVEAQPPWLPGLEARYMAF
AHDLMADAQRQDRPFFLYYASHHTHYPQFSGQSFAERSGRGPFGDSLMELDAAVGTLMTAIGDLG
LLEETLVIFTADNGPETMRMSRGGCSGLLRCGKGTTYEGGVREPALAFWPGHIAPGVTHELASSL
DLLPTLAALAGAPLPNVTLDGFDLSPLLLGTGKSPRQSLFFYPSYPDEVRGVFAVRSGKYKAHFF
TQGSAHSDTTADPACHASSSLTAHEPPLLYDLSKDPGENYNLLGGVAGATPEVLQALKQLQLLKA
QLDAAVTFGPSQVARGEDPALQICCHPGCTPRPACCHCPDPHA

METHODS AND COMPOSITIONS FOR INCREASING ARYLSULFATASE A ACTIVITY IN THE CNS

CROSS-REFERENCE TO RELATED APPLICATION

This application claims the benefit under 35 U.S.C. §119 (e) of U.S. Provisional Application No. 61/566,497, filed Dec. 2, 2011, which is incorporated herein in its entirety.

The instant application contains a Sequence Listing which has been submitted in ASCII format via EFS-Web and is hereby incorporated by reference in its entirety. Said ASCII copy, created on Jul. 3, 2013, is named 28570-711-311.txt and is 28 Kilobytes in size.

BACKGROUND OF THE INVENTION

Metachromatic leukodystrophy (MLD) is an inherited metabolic disease caused by a defect in the lysosomal enzyme arylsulfatase A (ASA), which functions to degrade sulfatides. An insufficient level of ASA causes a pathological buildup of 3-O-sulfogalactosyl ceramide (sulfatide), a sphingolipid, in, e.g., peripheral tissues, and the central nervous system (CNS). Symptoms including neurodegeneration and mental retardation appear during childhood; and early death can occur due to organ damage in the brain. Typically, treatment would include intravenous enzyme replacement therapy with recombinant ASA. However, systemically administered recombinant ASA does not cross the blood brain barrier (BBB), and therefore has little impact on the effects of the disease in the CNS.

SUMMARY OF THE INVENTION

Described herein are methods and compositions for treating a subject suffering from an arylsulfatase A ("ASA") deficiency. In certain embodiments, the methods allow delivery of ASA to the CNS by systemically administering a therapeutically effective amount of a bifunctional IgG-ASA fusion protein, where the IgG is an antibody (Ab) that binds an endogenous BBB receptor, such as the human insulin receptor (HIR). In certain embodiments, the HIR Ab-ASA fusion antibody binds to the extracellular domain of the insulin receptor and is transported across the blood brain barrier ("BBB") into the CNS, while retaining ASA enzyme activity. The HIR Ab binds to the endogenous insulin receptor on the BBB, and acts as a molecular Trojan horse to ferry the ASA into the brain. In certain embodiments, a therapeutically effective systemic dose of a HIR Ab-ASA fusion antibody for systemic administration is based, in part, on the specific CNS uptake characteristics of the fusion antibody from peripheral blood as described herein.

In one aspect provided herein is a method for treating an ASA deficiency in the central nervous system of a subject in need thereof, comprising systemically administering to the subject a therapeutically effective dose of a fusion antibody having ASA activity. In some embodiments of this aspect: (i) the fusion antibody comprises the amino acid sequence of an immunoglobulin heavy chain, the amino acid sequence of an ASA, and the amino acid sequence of an immunoglobulin light chain; (ii) the fusion antibody binds to an extracellular domain of the human insulin receptor and catalyzes hydrolysis of the cerebroside-sulfate groups of sphingolipids; and (iii) the amino acid sequence of the ASA is covalently linked to the carboxy terminus of the amino acid sequence of the immunoglobulin heavy chain.

In some embodiments at least about 100 ug of ASA enzyme are delivered to the human brain. In some embodiments, the therapeutically effective dose of the fusion antibody comprises at least about 0.5 mg/Kg of body weight. In some embodiments, systemic administration is parenteral, intravenous, subcutaneous, intra-muscular, trans-nasal, intra-arterial, transdermal, or respiratory.

In some embodiments, the brain uptake of the fusion antibody is at least 2 fold, 3 fold, 4, fold, 5 fold, 6 fold, 7 fold, 8 fold, 9 fold, 10 fold, 15 fold, 20 fold, 25 fold greater than the brain uptake of a control antibody. In some embodiments, the brain volume of distribution of the fusion antibody is at least 2 fold, 3 fold, 4, fold, 5 fold, 6 fold, 7 fold, 8 fold, 9 fold, 10 fold, 15 fold, 20 fold, 25 fold greater than the brain uptake of a control antibody.

In some embodiments, the fusion antibody is a chimeric antibody.

In some embodiments, the immunoglobulin heavy chain of the fusion antibody comprises a CDR1 corresponding to the amino acid sequence of SEQ ID NO:1 with up to 4 single amino acid mutations, a CDR2 corresponding to the amino acid sequence of SEQ ID NO:2 with up to 6 single amino acid mutations, or a CDR3 corresponding to the amino acid sequence of SEQ ID NO:3 with up to 3 single amino acid mutations, wherein the single amino acid mutations are substitutions, deletions, or insertions.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with up to 3 single amino acid mutations.

In other embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In further embodiments, the complementarity determining region of the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3, wherein the amino acid sequences comprise 1, 2, 3, 4, 5, or 6 single amino acid mutations.

In some embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, or a CDR3 corresponding to the amino acid sequence of SEQ ID NO:6 with up to 5 single amino acid mutations, wherein the single amino acid mutations are substitutions, deletions, or insertions.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, and a CDR3 corresponding to the amino acid sequence of SEQ ID NO:6 with up to 5 single amino acid mutations.

In other embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In further embodiments, the complementarity determining region of the immunoglobulin light chain of the fusion antibody comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6, wherein the amino acid sequences comprise 1, 2, 3, 4, 5, or 6 single amino acid mutations.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3; and the immunoglobulin light chain comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody is at least 90% identical to SEQ ID NO:7 and the amino acid sequence of the light chain immunoglobulin is at least 90% identical to SEQ ID NO:8.

In some embodiments, the immunoglobulin heavy chain of the fusion antibody comprises SEQ ID NO:7 and the amino acid sequence of the light chain immunoglobulin comprises SEQ ID NO:8

In yet further embodiments, the ASA comprises an amino acid sequence at least 90% (e.g., 95%, or 100%) identical to SEQ ID NO:9.

In other embodiments, the amino acid sequence of the immunoglobulin heavy chain of the fusion antibody at least 90% identical to SEQ ID NO:7; the amino acid sequence of the light chain immunoglobulin is at least 90% identical to SEQ ID NO:8; and the amino acid sequence of the ASA is at least 95% identical to SEQ ID NO:9 or comprises SEQ ID NO:9.

In still other embodiments, the amino acid sequence of the immunoglobulin heavy chain of the fusion antibody comprises SEQ ID NO:7, the amino acid sequence of the immunoglobulin light chain comprises SEQ ID NO:8, and the amino acid sequence of the ASA comprises SEQ ID NO:9

In a further aspect provided herein is a method for treating an ASA deficiency in the central nervous system of a subject in need thereof, comprising systemically administering to the subject a therapeutically effective dose of a fusion antibody having ASA activity, wherein: (i) the fusion antibody comprises: (a) a fusion protein at least 95% identical to SEQ ID NO:10, and (b) an immunoglobulin light chain; and (ii) the fusion antibody binds to an extracellular domain of the human insulin receptor and catalyzes hydrolysis of linkages in sulfatide sphingomyelins.

In some embodiments, a fusion protein comprising the amino acid sequences of an immunoglobulin heavy chain and an arylsulfatase A comprises an amino acid sequence that is at least 80%, 85%, 90%, 95%, 96%, 97%, 98%, or 99% identical to SEQ ID NO:10.

In yet another aspect provided herein is a method for treating an ASA deficiency in the central nervous system of a subject in need thereof, comprising systemically administering to the subject a therapeutically effective dose of a fusion antibody having ASA activity, wherein:
(i) the fusion antibody comprises a fusion protein containing the amino acid sequence of an immunoglobulin heavy chain and an ASA or comprises a fusion protein containing the amino acid sequence of an immunoglobulin light chain and an ASA; the fusion antibody binds to the extracellular domain of the human insulin receptor; and the fusion antibody catalyzes hydrolysis of linkages in sulfatide sphingomyelin; and (ii) the amino acid sequence of the ASA is covalently linked to the carboxy terminus of the amino acid sequence of the immunoglobulin heavy chain or the immunoglobulin light chain.

In some embodiments, the ASA deficiency in the central nervous system is metachromatic leukodystrophy (MLD).

In certain embodiments, provided herein is a fusion antibody comprising: (a) a fusion protein comprising the amino acid sequences of an immunoglobulin heavy chain and an arylsulfatase A, and (b) an immunoglobulin light chain; wherein the fusion antibody crosses the blood brain barrier (BBB) and catalyzes hydrolysis of 2-sulfate groups of cerebroside sulfate esters and sulfatide sphingolipids.

In some embodiments, the amino acid sequence of the arylsulfatase A is covalently linked to the carboxy terminus of the amino acid sequence of the immunoglobulin heavy chain.

In some embodiments, the fusion antibody is post-translationally modified by a sulfatase modifying factor type 1 (SUMF1).

In some embodiments, the fusion antibody comprises a formylglycine.

In some embodiments, the fusion protein further comprises a linker between the amino acid sequence of the arylsulfatase A and the carboxy terminus of the amino acid sequence of the immunoglobulin heavy chain.

In some embodiments, the arylsulfatase A specific activity of the fusion antibody is at least about 10 units/mg.

In some embodiments, the ASA retains at least 20% of its activity compared to its activity as a separate entity. In some embodiments, the ASA and the immunoglobulin each retains at least 20% of its activity, on a molar basis, compared to its activity as a separate entity.

In some embodiments, the immunoglobulin heavy chain is an immunoglobulin heavy chain of IgG. In some embodiments, the immunoglobulin heavy chain comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In some embodiments, the immunoglobulin light chain is an immunoglobulin light chain of kappa class. In some embodiments, the immunoglobulin light chain is an immunoglobulin light chain of lambda class. In some embodiments, the immunoglobulin light chain comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In some embodiments, the fusion antibody crosses the BBB by binding an endogenous BBB receptor-mediated transport system. In some embodiments, the fusion antibody crosses the BBB via an endogenous BBB receptor selected from the group consisting of the insulin receptor, transferrin receptor, leptin receptor, lipoprotein receptor, and the IGF receptor. In some embodiments, the fusion antibody crosses the BBB by binding an insulin receptor.

In certain embodiments, provided herein is a pharmaceutical composition comprising a therapeutically effective amount of a fusion antibody described herein, and a pharmaceutically acceptable excipient.

In some embodiments, provided herein is an isolated polynucleotide encoding the fusion antibody described herein. In some embodiments, the isolated polynucleotide comprises the nucleic acid sequence of SEQ ID NO:14.

In some embodiments, provided herein is a vector comprising the isolated polynucleotide described herein. In some embodiments, the vector provided herein comprises the nucleic acid sequence of SEQ ID NO:14.

In some embodiments, provided herein is a host cell comprising the vector described herein. In some embodiments, the host cell is a Chinese Hamster Ovary (CHO) cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, as follow:

FIG. 5. Amino acid sequence of an immunoglobulin heavy chain variable region from an exemplary human insulin receptor antibody directed against the extracellular domain of the human insulin receptor. The underlined sequences are a signal peptide, CDR1, CDR2, and CDR3, respectively. The heavy chain constant region, taken from human IgG1, is shown in italics.

FIG. 6. Amino acid sequence of an immunoglobulin light chain variable region from an exemplary human insulin receptor antibody directed against the extracellular domain of the human insulin receptor. The underlined sequences are a signal peptide, CDR1, CDR2, and CDR3, respectively. The constant region, derived from human kappa light chain, is shown in italics.

FIG. 7. A table showing the CDR1, CDR2, and CDR3 amino acid sequences from a heavy and light chain of an exemplary human insulin receptor antibody directed against the extracellular domain of the human insulin receptor.

FIG. 8. Amino acid sequence of arylsulfatase A (ASA) (Swiss-Prot P15289), not including the initial 18 amino acid signal peptide (mature ASA).

FIG. 9. Amino acid sequence of a fusion of an exemplary human insulin receptor antibody heavy chain to mature human ASA. The underlined sequences are, in order, an IgG signal peptide, CDR1, CDR2, CDR3, and a peptide linker (Ser-Ser-Ser) linking the carboxy terminus of the heavy chain to the amino terminus of the ASA. Sequence in italic corresponds to the heavy chain constant region, taken from human IgG1. The sequence in bold corresponds to human ASA.

DETAILED DESCRIPTION OF THE INVENTION

Figure 1:
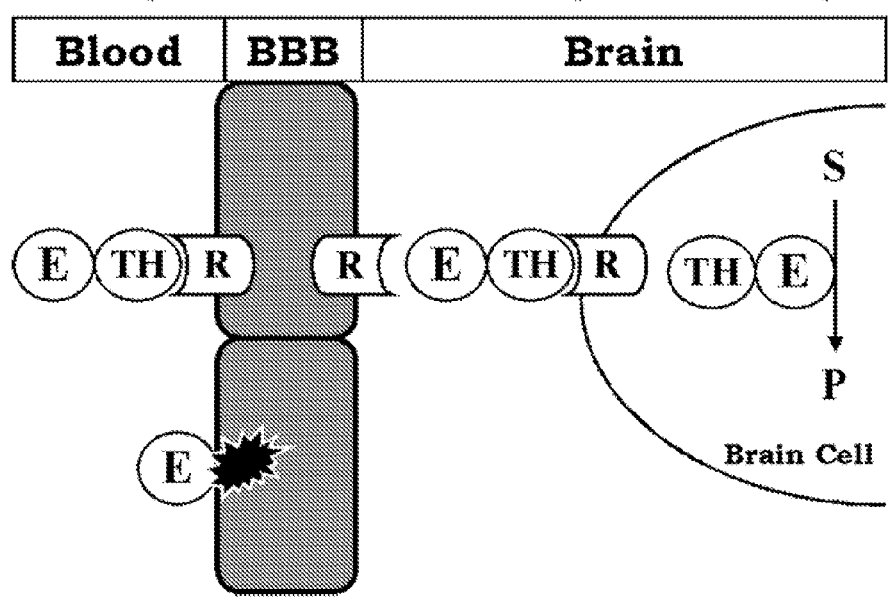
FIG. 1. Schematic depiction of a "molecular trojan horse" strategy in which the fusion antibody comprises an antibody to the extracellular domain of an endogenous BBB receptor (R), which acts as a molecular Trojan horse (TH), and ASA, a lysosomal enzyme (E). Once inside brain cells, behind the BBB, the ASA part of the fusion antibody then converts sulfatides (S) to degradable products (P).

The blood brain barrier (BBB) is a severe impediment to the delivery of systemically administered ASA (e.g., recombinant ASA) to the central nervous system. The methods and compositions described herein address three factors that are important in delivering a therapeutically significant level of ASA activity across the BBB to the CNS: 1) Modification of an ASA to allow it to cross the BBB via transport on an endogenous BBB transporter; 2) the amount and rate of uptake of systemically administered modified ASA into the CNS, via retention of ASA activity following the modification required to produce BBB transport. Various aspects of the methods and compositions described herein address these factors, by (1) providing human insulin receptor (HIR) antibody (Ab)-ASA fusion antibodies comprising an ASA (i.e., a protein having ASA activity) fused, with or without intervening sequence, to an immunoglobulin (heavy chain or light chain) directed against the extracellular domain of a human insulin receptor; and (2) establishing therapeutically effective systemic doses of the fusion antibodies based on the uptake in the CNS and the specific activity.

Accordingly, the invention provides compositions and methods for treating a ASA deficiency in the central nervous system by systemically administering to a subject in need thereof a therapeutically effective dose of a bifunctional HIR Ab-ASA fusion antibody having ASA activity and selectively binding to the extracellular domain of an endogenous BBB receptor transporter such as the human insulin receptor.

DEFINITIONS

"Treatment" or "treating" as used herein includes achieving a therapeutic benefit and/or a prophylactic benefit. By therapeutic benefit is meant eradication or amelioration of the underlying disorder or condition being treated. For example, in an individual with MLD, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a lysosomal storage disorder), or decreasing the likelihood of occurrence of a condition. As used herein, "treating" or "treatment" includes prophylaxis.

As used herein, the term "effective amount" can be an amount, which when administered systemically, is sufficient to effect beneficial or desired results in the CNS, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions include, but are not limited to, mental retardation, hearing loss, and neurodegeneration. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the ASA specific activity of the HIR Ab-ASA fusion antibody administered, its absorption profile (e.g., its rate of uptake into the brain), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal In some embodiments a "subject" or an "individual" is a human. In some embodiments, the subject suffers from MLD.

In some embodiments, a pharmacological composition comprising an HIRMAb-ASA fusion antibody is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins Pa., USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and proteins are well known in the art.

The Blood Brain Barrier

In one aspect, the invention provides compositions and methods that utilize a ASA fused to an immunoglobulin capable of crossing the blood brain barrier (BBB) via receptor-mediated transport on an endogenous BBB receptor/transporter. A preferred endogenous transporter for targeting is the insulin receptor on the BBB. The BBB insulin receptor mediates the transport of circulating insulin into the brain, as well as certain peptidomimetic monoclonal antibodies (MAb) such as the HIRMAb. Other endogenous transporters that might be targeted with either an endogenous ligand or a peptidomimetic MAb include the BBB transferrin receptor, the BBB insulin-like growth factor receptor, the BBB leptin receptor, or the BBB low density lipoprotein receptor. The compositions and methods are useful in transporting ASA from the peripheral blood and across the blood brain barrier into the CNS. As used herein, the "blood-brain barrier" refers to the barrier between the peripheral circulation and the brain and spinal cord which is formed by tight junctions within the brain capillary endothelial plasma membranes and creates an extremely tight barrier that restricts the transport of molecules into the brain; the BBB is so tight that it is capable of restricting even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB limits the development of new neurotherapeutics, diagnostics, and research tools for the brain and CNS. Most large molecule therapeutics such as recombinant proteins, antisense drugs, gene medicines, purified antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers ASA only to the ependymal surface of the brain, not into brain parenchyma, which is typical for drugs given by the ICV route. The IC administration of an enzyme such as ASA, only provides local delivery, owing to the very low efficiency of protein diffusion within the brain. The CED results in preferential fluid flow through the white matter tracts of brain, which causes demyelination, and astrogliosis.

The methods described herein offer an alternative to these highly invasive and generally unsatisfactory methods for bypassing the BBB, allowing a functional ASA to cross the BBB from the peripheral blood into the CNS following systemic administration of an HIRMAb-ASA fusion antibody composition described herein. The methods described herein exploit the expression of insulin receptors (e.g., human insulin receptors) on the BBB to shuttle a desired bifunctional HIRMAb-ASA fusion antibody from peripheral blood into the CNS.

Endogenous Receptors

Certain endogenous small molecules in blood, such as glucose or amino acids, are water soluble, yet are able to penetrate the BBB, owing to carrier-mediated transport (CMT) on certain BBB carrier systems. For example, glucose penetrates the BBB via CMT on the GLUT1 glucose transporter Amino acids, including therapeutic amino acids such as L-DOPA, penetrate the BBB via CMT on the LAT1 large neutral amino acid transporter. Similarly, certain endogenous large molecules in blood, such as insulin, transferrin, insulin-like growth factors, leptin, or low density lipoprotein are able to penetrate the BBB, owing to receptor-mediated transcytosis (RMT) on certain BBB receptor systems. For example, insulin penetrates the BBB via RMT on the insulin receptor. Transferrin penetrates the BBB via RMT on the transferrin receptor. Insulin-like growth factors may penetrate the BBB via RMT on the insulin-like growth factor receptor. Leptin may penetrate the BBB via RMT on the leptin receptor. Low density lipoprotein may penetrate the BBB via transport on the low density lipoprotein receptor.

The BBB has been shown to have specific receptors, including insulin receptors, that allow the transport from the blood to the brain of several macromolecules. In particular, insulin receptors are suitable as transporters for the HIR Ab-ASA fusion antibodies described herein. The HIR-ASA fusion antibodies described herein bind to the extracellular domain (ECD) of the human insulin receptor.

Insulin receptors and their extracellular, insulin binding domain (ECD) have been extensively characterized in the art both structurally and functionally. See, e.g., Yip et al (2003), *J Biol. Chem*, 278(30):27329-27332; and Whittaker et al. (2005), *J Biol Chem*, 280(22):20932-20936. The amino acid and nucleotide sequences of the human insulin receptor can be found under GenBank accession No. NM_000208.

Antibodies that Bind to an Insulin Receptor-Mediated Transport System

One noninvasive approach for the delivery of ASA to the CNS is to fuse the ASA to an antibody that selectively binds to the ECD of the insulin receptor. Insulin receptors expressed on the BBB can thereby serve as a vector for transport of the ASA across the BBB. Certain ECD-specific antibodies may mimic the endogenous ligand and thereby traverse a plasma membrane barrier via transport on the specific receptor system. Such insulin receptor antibodies act as molecular "Trojan horses," or "TH" as depicted schematically in FIG. 1. By itself, ASA normally does not cross the blood-brain barrier (BBB). However, following fusion of the ASA to the TH, the enzyme is able to cross the BBB, and the brain cell membrane, by trafficking on the endogenous BBB receptor such as the IR, which is expressed at both the BBB and brain cell membranes in the brain (FIG. 1).

Thus, despite the fact that antibodies and other macromolecules are normally excluded from the brain, they can be an effective vehicle for the delivery of molecules into the brain parenchyma if they have specificity for the extracellular domain of a receptor expressed on the BBB, e.g., the insulin receptor. In certain embodiments, an HIR Ab-ASA fusion antibody binds an exofacial epitope on the human BBB HIR and this binding enables the fusion antibody to traverse the BBB via a transport reaction that is mediated by the human BBB insulin receptor.

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable domain" refers to protein domains that differ extensively in sequence among family members (i.e., among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR". The variable domains of unmodified heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs", which directly bind, in a complementary manner, to an antigen and are known as CDR1, CDR2, and CDR3 respectively.

In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.* 196:901 917 (1987)).

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR comprises, consist essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. The VFR can form a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("$\kappa$") and lambda or ("$\lambda$"), based on the amino acid sequences of their constant domains.

In referring to an antibody or fusion antibody described herein, the terms "selectively bind," "selectively binding," "specifically binds," or "specifically binding" refer to binding to the antibody or fusion antibody to its target antigen for which the dissociation constant (Kd) is about $10^{-6}$ M or lower, i.e., $10^{-7}$, $10^{-8}$, $10^{-9}$, $10^{-10}$, $10^{-11}$, or $10^{-12}$M.

The term antibody as used herein will also be understood to mean one or more fragments of an antibody that retain the ability to specifically bind to an antigen, (see generally, Holliger et al., *Nature Biotech.* 23 (9) 1126-1129 (2005)). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423 426; and Huston et al. (1988) *Proc. Natl. Acad. Sci. USA* 85:5879 5883; and Osbourn et al. (1998) *Nat. Biotechnol.* 16:778). Such single chain antibodies are also intended to be encompassed within the term antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CH$\gamma$1 ($\gamma$1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in The Pharmacology of Monoclonal Antibodies, Vol. 113, Rosenburg and Moore eds. Springer-Verlag, New York, pp. 269 315 (1994).

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a HIR Ab is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse, or 100% human. A more highly humanized form of the HIR MAb can also be engineered, and the humanized HIR Ab has activity comparable to the murine HIR Ab and can be used in embodiments of the invention. See, e.g., U.S. Patent Application Publication Nos. 20040101904, filed Nov. 27, 2002 and 20050142141, filed Feb. 17, 2005. Humanized antibodies to the human BBB insulin receptor with sufficient human sequences for use in the invention are described in, e.g., Boado et al. (2007), *Biotechnol Bioeng*, 96(2):381-391.

In exemplary embodiments, the HIR antibodies or HIR-ASA fusion antibodies derived therefrom contain an immunoglobulin heavy chain comprising CDRs corresponding to the sequence of at least one of the HC CDRs listed in FIG. 7 (SEQ ID NOs 1-3) or a variant thereof. For example, a HC CDR1 corresponding to the amino acid sequence of SEQ ID NO:1 with up to 1, 2, 3, 4, 5, or 6 single amino acid mutations, a HC CDR2 corresponding to the amino acid sequence of SEQ ID NO:2 with up to 1, 2, 3, 4, 5, 6, 7, 8, 9, or 10 single amino acid mutations, or a HC CDR3 corresponding to the amino acid sequence of SEQ ID NO:3 with up to 1, or 2 single amino acid mutations, where the single amino acid mutations are substitutions, deletions, or insertions.

In other embodiments, the HIR Abs or HIR Ab-ASA fusion Abs contain an immunoglobulin HC the amino acid sequence of which is at least 50% identical (i.e., at least, 55, 60, 65, 70, 75, 80, 85, 90, 95, or any other percent up to 100% identical) to SEQ ID NO:7 (shown in FIG. 5).

In some embodiments, the HIR Abs or HIR Ab-ASA fusion Abs include an immunoglobulin light chain comprising CDRs corresponding to the sequence of at least one of the LC CDRs listed in FIG. 7 (SEQ ID NOs: 4-6) or a variant thereof. For example, a LC CDR1 corresponding to the amino acid sequence of SEQ ID NO:4 with up to 1, 2, 3, 4, or 5 single amino acid mutations, a LC CDR2 corresponding to the amino acid sequence of SEQ ID NO:5 with up to 1, 2, 3, or 4 single amino acid mutations, or a LC CDR3 corresponding to the amino acid sequence of SEQ ID NO:6 with up to 1, 2, 3, 4, or 5 single amino acid mutations.

In other embodiments, the HIR Abs or HIR Ab-ASA fusion Abs contain an immunoglobulin LC the amino acid sequence of which is at least 50% identical (i.e., at least, 55, 60, 65, 70, 75, 80, 85, 90, 95, or any other percent up to 100% identical) to SEQ ID NO:8 (shown in FIG. 6).

In yet other embodiments, the HIR Abs or HIR Ab-ASA fusion Abs contain both a heavy chain and a light chain corresponding to any of the above-mentioned HIR heavy chains and HIR light chains.

HIR antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

One of ordinary skill in the art will appreciate that current technologies permit a vast number of sequence variants of candidate HIR Abs or known HIR Abs to be readily generated be (e.g., in vitro) and screened for binding to a target antigen such as the ECD of the human insulin receptor or an isolated epitope thereof. See, e.g., Fukuda et al. (2006) "In vitro evolution of single-chain antibodies using mRNA display," *Nuc. Acid Res.*, 34(19) (published online) for an example of ultra high throughput screening of antibody sequence variants. See also, Chen et al. (1999), "In vitro scanning saturation mutagenesis of all the specificity determining residues in an antibody binding site," *Prot Eng*, 12(4): 349-356. An insulin receptor ECD can be purified as described in, e.g., Coloma et al. (2000) *Pharm Res*, 17:266-274, and used to screen for HIR Abs and HIR Ab sequence variants of known HIR Abs.

Accordingly, in some embodiments, a genetically engineered HIR Ab, with the desired level of human sequences, is fused to an ASA, to produce a recombinant fusion antibody that is a bi-functional molecule. The HIR Ab-ASA fusion antibody: (i) binds to an extracellular domain of the human insulin receptor; (ii) catalyzes hydrolysis of linkages in sulfatides; and (iii) is able to cross the BBB, via transport on the BBB HIR, and retain ASA activity once inside the brain, following peripheral administration.

Arylsulfatase A (ASA)

Systemic administration (e.g., by intravenous injection) of recombinant ASA fails to rescue a deficiency of ASA in the CNS of patients suffering from MLD. ASA does not cross the BBB, and the lack of transport of the enzyme across the BBB prevents it from having a significant therapeutic effect in the CNS following peripheral administration. However, when the ASA is fused to an HIR Ab (e.g., by a covalent linker), this enzyme is now able to enter the CNS from blood following a non-invasive peripheral route of administration such as intravenous, intra-arterial, intramuscular, subcutaneous, intraperitoneal, or even oral administration. Administration of a HIR Ab-ASA fusion antibody enables delivery of ASA activity into the brain from peripheral blood. Described herein is the determination of a systemic dose of the HIR Ab-ASA fusion antibody that is therapeutically effective for treating an ASA deficiency in the CNS. As described herein, appropriate systemic doses of an HIR Ab-ASA fusion antibody are established based on a quantitative determination of CNS uptake characteristics and enzymatic activity of an HIR Ab-enzyme fusion antibody. Sulfatides are sulfated galactosylceramides synthesized primarily in the oligodendrocytes in the central nervous system. As used herein, ASA (e.g., the human ASA sequence listed under GenBank Accession No. NP_000478; Swiss-Prot P15289) refers to any naturally occurring or artificial enzyme that can catalyze the hydrolysis of cerebroside 3-sulfate into cerebroside and sulfate.

ASA is a member of a family of sulfatases that requires a specific post-translational modification for expression of ASA enzyme activity. The activity of the ASA enzyme is activated following the conversion of Cys-69 (of the intact ASA protein including the signal peptide) to a formylglycine residue by a sulfatase modifying factor type 1 (SUMF1), which is also called the formylglycine generating enzyme (FGE). In some embodiments, the fusion antibody comprising ASA is post-translationally modified by a sulfatase modifying factor type 1 (SUMF1). In some embodiments, the post-translational modification comprises a cysteine to formylglycine conversion. In some embodiments, the fusion antibody comprises an ASA that comprises a formylglycine residue.

In some embodiments, ASA has an amino acid sequence that is at least 50% identical (i.e., at least, 55, 60, 65, 70, 75, 80, 85, 90, 95, or any other percent up to 100% identical) to the amino acid sequence of human ASA, a 507 amino acid protein listed under Swiss-Prot P15289, or a 489 amino acid subsequence thereof, which lacks a 18 amino acid signal peptide, and corresponds to SEQ ID NO:9 (FIG. 8). The structure-function relationship of human ASA is well established, as described in, e.g., von Bulow et al. (2006), "Crystal structure of an enzyme-substrate complex provides insight into the interaction between human arylsulfatase a and its substrates during catalysis," *J. Mol. Biol.*, 305: 26-277, 2001. In particular, residues that are critical to the function of ASA include, e.g., Cys-69, Lys-123, Ser-150, His-229, and Lys-302.

In some embodiments, ASA has an amino acid sequence at least 50% identical (i.e., at least, 55, 60, 65, 70, 75, 80, 85, 90, 95, or any other percent up to 100% identical) to SEQ ID NO:9 (shown in FIG. 8). Sequence variants of a canonical ASA sequence such as SEQ ID NO:9 can be generated, e.g., by random mutagenesis of the entire sequence or specific subsequences corresponding to particular domains. Alternatively, site directed mutagenesis can be performed reiteratively while avoiding mutations to residues known to be critical to ASA function such as those given above. Further, in generating multiple variants of an ASA sequence, mutation tolerance prediction programs can be used to greatly reduce the number of non-functional sequence variants that would be generated by strictly random mutagenesis. Various programs) for predicting the effects of amino acid substitutions in a protein sequence on protein function (e.g., SIFT, PolyPhen, PANTHER PSEC, PMUT, and TopoSNP) are described in, e.g., Henikoff et al. (2006), "Predicting the Effects of Amino Acid Substitutions on Protein Function," *Annu. Rev. Genomics Hum. Genet.*, 7:61-80. ASA sequence variants can be screened for of ASA activity/retention of ASA activity by p-nitrocatechol sulfate (NCS) spectrophotometric ASA assays known in the art. One unit of ASA activity is defined as the hydrolysis of 1 umole substrate/min at 37 C. at a defined substrate concentration and reaction conditions. Accordingly, one of ordinary skill in the art will appreciate that a very large number of operable ASA sequence variants can be obtained by generating and screening extremely diverse "libraries" of ASA sequence variants by methods that are routine in the art, as described above.

Percent sequence identity is determined by conventional methods. See, for example, Altschul et al., Bull. Math. Bio. 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:9 or SEQ ID NO: 16) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM *J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present invention also includes proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

Compositions

It has been found that the bifunctional HIR Ab-ASA fusion antibodies described herein, retain a high proportion of the activity of their separate constituent proteins, i.e., binding of the HIR Ab to the IR ECD, and the enzymatic activity of ASA. Construction of cDNAs and expression vectors encoding any of the proteins described herein, as well as their expression and purification are well within those of ordinary skill in the art, and are described in detail herein in, e.g., Examples 1-3, and, in Boado et al (2007), *Biotechnol Bioeng* 96:381-391, U.S. patent application Ser. No. 11/061,956, and U.S. patent application Ser. No. 11/245,710.

Described herein are bifunctional HIR Ab-ASA fusion antibodies containing a HIR Ab, as described herein, capable of crossing the BBB fused to ASA, where the HIR Ab is capable of crossing the blood brain barrier and the ASA each retain an average of at least about 10, 20, 30, 40, 50, 60, 70, 80, 90, 95, 99, or 100% of their activities, compared to their activities as separate entities. In some embodiments, the invention provides a HIR Ab-ASA fusion antibody where the HIR Ab and ASA each retain an average of at least about 50% of their activities, compared to their activities as separate entities. In some embodiments, the invention provides a HIR Ab-ASA fusion antibody where the HIR Ab and ASA each retain an average of at least about 60% of their activities, compared to their activities as separate entities. In some embodiments, the invention provides a HIR Ab-ASA fusion antibody where the HIR Ab and ASA each retain an average of at least about 70% of their activities, compared to their activities as separate entities. In some embodiments, the invention provides a HIR Ab-ASA fusion antibody where the HIR Ab and ASA each retain an average of at least about 80% of their activities, compared to their activities as separate entities. In some embodiments, the invention provides a fusion HIR Ab-ASA fusion antibody where the HIR Ab and ASA each retain an average of at least about 90% of their activities, compared to their activities as separate entities. In some embodiments, the HIR Ab retains at least about 10, 20, 30, 40, 50, 60, 70, 80, 90, 95, 99, or 100% of its activity, compared to its activity as a separate entity, and the ASA retains at least about 10, 20, 30, 40, 50, 60, 70, 80, 90, 95, 99, or 100% of its activity, compared to its activity as a separate entity. Accordingly, described herein are compositions containing a bifunctional HIR Ab-ASA fusion antibody capable of crossing the BBB, where the constituent HIR Ab and ASA each retain, as part of the fusion antibody, an average of at least about 10, 20, 30, 40, 50, 60, 70, 80, 90, 95, 99, or 100% of their activities, i.e., HIR binding and ASA activity, respectively, compared to their activities as separate proteins. An HIR Ab ASA fusion antibody refers to a fusion protein comprising any of the HIR antibodies and ASA described herein.

In the HIR Ab-ASA fusion antibodies described herein, the covalent linkage between the antibody and the ASA may be to the carboxy or amino terminal of the HIR antibody and the amino or carboxy terminal of the ASA as long as the linkage allows the HIR Ab-ASA fusion antibody to bind to the ECD of the IR and cross the blood brain barrier, and allows the ASA to retain a therapeutically useful portion of its activity. In certain embodiments, the covalent link is between an HC of the antibody and the ASA or a LC of the antibody and the ASA. Any suitable linkage may be used, e.g., carboxy terminus of light chain to amino terminus of ASA, carboxy terminus of heavy chain to amino terminus of ASA, amino terminus of light chain to amino terminus of ASA, amino terminus of heavy chain to amino terminus of ASA, carboxy terminus of light chain to carboxy terminus of ASA, carboxy terminus of heavy chain to carboxy terminus of ASA, amino terminus of light chain to carboxy terminus of ASA, or amino terminus of heavy chain to carboxy terminus of ASA. In some embodiments, the linkage is from the carboxy terminus of the HC to the amino terminus of the ASA.

The ASA may be fused, or covalently linked, to the targeting antibody (e.g., MAb, HIR-MAb) through a linker. A linkage between terminal amino acids can be accomplished by an intervening peptide linker sequence that forms part of the fused amino acid sequence. The peptide sequence linker may be 0, 1, 2, 3, 4, 5, 6, 7, 8, 9, 10, or more than 10 amino acids in length. In some embodiments, including some preferred embodiments, the peptide linker is less than 20, 15, 14, 13, 12, 11, 10, 9, 8, 7, 6, 5, 4, 3, 2, or 1 amino acids in length. In some embodiments, including some preferred embodiments, the peptide linker is at least 0, 1, 2, 3, 4, 5, 6, 7, 8, 9, 10 amino acids in length. In some embodiments, the ASA is directly linked to the targeting antibody, and is therefore 0 amino acids in length. In some embodiments, there is no linker linking the ASA to the targeting antibody.

In some embodiments, the linker comprises glycine, serine, and/or alanine residues in any combination or order. In some cases, the combined percentage of glycine, serine, and alanine residues in the linker is at least 5%, 10%, 15%, 20%, 25%, 30%, 40%, 50%, 60%, 70%, 75%, 80%, 90%, or 95% of the total number of residues in the linker. In some preferred embodiments, the combined percentage of glycine, serine, and alanine residues in the linker is at least 50%, 60%, 70%, 75%, 80%, 90%, or 95% of the total number of residues in the linker. In some embodiments, any number of combinations of amino acids (including natural or synthetic amino acids) can be used for the linker. In some embodiments, a three amino acid linker is used. In some embodiments, the linker has the sequence Ser-Ser-Ser. In some embodiments, a two amino acid linker comprises glycine, serine, and/or alanine residues in any combination or order (e.g., Gly-Gly, Ser-Gly, Gly-Ser, Ser-Ser. Ala-Ala, Ser-Ala, or Ala-Ser linker). In some embodiments, a two amino acid linker consists of one glycine, serine, and/or alanine residue along with another amino acid (e.g., Ser-X, where X is any known amino acid). In still other embodiments, the two-amino acid linker consists of any two amino acids (e.g., X-X), exept gly, ser, or ala.

As described herein, in some embodiments a linker that is greater than two amino acids in length. Such linker may also comprise glycine, serine, and/or alanine residues in any combination or order, as described further herein. In some embodiments, the linker consists of one glycine, serine, and/or alanine residue along with other amino acids (e.g., Ser-nX, where X is any known amino acid, and n is the number of amino acids). In still other embodiments, the linker consists of any two amino acids (e.g., X-X). In some embodiments, said any two amino acids are Gly, Ser, or Ala, in any combination or order, and within a variable number of amino acids intervening between them. In an example of an embodiment, the linker consists of at least one Gly. In an example of an embodiment, the linker consists of at least one Ser. In an example of an embodiment, the linker consists of at least one Ala. In some embodiments, the linker consists of at least 1, 2, 3, 4, 5, 6, 7, 8, 9, or 10 Gly, Ser, and/or Ala residues. In preferred embodiments, the linker comprises Gly and Ser in repeating sequences, in any combination or number, such as $(Gly_4Ser)_3$, or other variations.

A linker for use in the present invention may be designed by using any method known in the art. For example, there are multiple publicly-available programs for determining optimal amino acid linkers in the engineering of fusion proteins. Publicly-available computer programs (such as the LINKER program) that automatically generate the amino acid sequence of optimal linkers based on the user's input of the sequence of the protein and the desired length of the linker may be used for the present methods and compositions. Often, such programs may use observed trends of naturally-occurring linkers joining protein subdomains to predict optimal protein linkers for use in protein engineering. In some cases, such programs use other methods of predicting optimal linkers. Examples of some programs suitable for predicting a linker for the present invention are described in the art, see, e.g., Xue et al. (2004) Nucleic Acids Res. 32, W562-W565 (Web Server issue providing internet link to LINKER program to assist the design of linker sequences for constructing functional fusion proteins); George and Heringa, (2003), Protein Engineering, 15(11):871-879 (providing an internet link to a linker program and describing the rational design of protein linkers); Argos, (1990), J. Mol. Biol. 211:943-958; Arai et al. (2001) Protein Engineering, 14(8):529-532; Crasto and Feng, (2000) Protein Engineering 13(5):309-312.

The peptide linker sequence may include a protease cleavage site, however this is not a requirement for activity of the ASA; indeed, an advantage of these embodiments of the present invention is that the bifunctional HIR Ab-ASA fusion antibody, without cleavage, is partially or fully active both for transport and for activity once across the BBB. FIG. 9 shows an exemplary embodiment of the amino acid sequence of a HIR Ab-ASA fusion antibody (SEQ ID NO:10) in which the HC is fused through its carboxy terminus via a three amino acid "ser-ser-ser" linker to the amino terminus of the ASA. In some embodiments, the fused ASA sequence is devoid of its 18 amino acid signal peptide, as shown in FIG. 9.

In some embodiments, a HIR Ab-ASA fusion antibody comprises both a HC and a LC. In some embodiments, the HIR Ab-ASA fusion antibody is a monovalent antibody. In other embodiments, the HIR Ab-ASA fusion antibody is a divalent antibody, as described herein in the Example section.

The HIR Ab used as part of the HIR Ab-ASA fusion antibody can be glycosylated or nonglycosylated; in some embodiments, the antibody is glycosylated, e.g., in a glycosylation pattern produced by its synthesis in a CHO cell.

As used herein, "activity" includes physiological activity (e.g., ability to cross the BBB and/or therapeutic activity), binding affinity of the HIR Ab for the IR ECD, or the enzymatic activity of ASA.

Transport of a HIR Ab-ASA fusion antibody across the BBB may be compared to transport across the BBB of the HIR Ab alone by standard methods. For example, pharmacokinetics and brain uptake of the HIR Ab-ASA fusion antibody by a model animal, e.g., a mammal such as a primate, may be used. Similarly, standard models for determining ASA activity may also be used to compare the function of the ASA alone and as part of a HIR Ab-ASA fusion antibody. See, e.g., Example 4, which demonstrates the enzymatic activity of ASA versus HIR Ab-ASA fusion antibody. Binding affinity for the IR ECD can be compared for the HIR Ab-ASA fusion antibody versus the HIR Ab alone. See, e.g., Example 4 herein.

Also included herein are pharmaceutical compositions that contain one or more HIR Ab-ASA fusion antibodies described herein and a pharmaceutically acceptable excipient. A thorough discussion of pharmaceutically acceptable carriers/excipients can be found in Remington's Pharmaceutical Sciences, Gennaro, A R, ed., 20th edition, 2000: Williams and Wilkins Pa., USA. Pharmaceutical compositions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the CNS uptake characteristics of a HIR Ab-ASA fusion antibody as described herein, and according to the subject to be treated, the state of the subject and the effect desired. The person responsible for administration will, in any event, determine the appropriate dose for the individual subject.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284, 262), transdermal administration (See U.S. Pat. Nos. 6,348, 210; and 6,322,808) and transmucosal administration (See U.S. Pat. No. 5,656,284). Such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Methods

Described herein are methods for delivering an effective dose of ASA to the CNS across the BBB by systemically administering a therapeutically effective amount of a HIR Ab-ASA fusion antibody, as described herein. Suitable systemic doses for delivery of a HIR Ab-ASA fusion antibody is based on its CNS uptake characteristics and ASA specific activity as described herein. Systemic administration of a HIR Ab-ASA fusion antibody to a subject suffering from an ASA deficiency is an effective approach to the non-invasive delivery of ASA to the CNS.

The amount of a HIR-ASA fusion antibody that is a therapeutically effective systemic dose of a HIR Ab-ASA fusion antibody depends, in part, on the CNS uptake characteristics of the HIR-ASA fusion antibody to be administered, as described herein, e.g., the percentage of the systemically administered dose to be taken up in the CNS, In some embodiments, 1% (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered HIR Ab-ASA fusion antibody is delivered to the brain as a result of its uptake from peripheral blood across the BBB. In some embodiments, at least 0.5%, (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered dose of the HIR Ab-ASA fusion antibody is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

Accordingly, in some embodiments the invention provides methods of administering a therapeutically effective amount of a HIR Ab-ASA fusion antibody systemically, such that the amount of the HIR Ab-ASA fusion antibody to cross the BBB provides at least 3 ng of ASA protein/mg protein in the subject's brain, e.g., 3, 5, 6, 7, 8, 9, 10, 12, 14, 16, 18, 20, 30, 40, 50 or any other value from 3 to 50 ng of ASA protein/mg protein in the subject's brain.

In some embodiments, the total number of units of ASA activity delivered to a subject's brain is at least, 0.5 milliunits per gram brain, e.g., at least 0.5, 0.6, 0.7, 0.8, 0.9, 1, 2, 3, 4, 5 or any other total number of ASA units from about 0.5 to 5 milliunits of ASA activity delivered per gram brain.

In some embodiments, a therapeutically effective systemic dose comprises at least 50, 100, 200, 300, 400, 500, 600, 700, 800, 900, 1000, 1500, 2000, 2500 units per brain, or any other systemic dose from about 50 to 2500 units of ASA activity per brain.

In other embodiments, a therapeutically effective systemic dose is at least about 10 units of ASA activity/kg body weight, at least about 10, 12, 15, 18, 25, 30, 50, 75, 100, 150, 200, 250, or any other number of ASA units from about 5 to 250 units of ASA activity/kg of body weight.

One of ordinary skill in the art will appreciate that the mass amount of a therapeutically effective systemic dose of a HIR Ab-ASA fusion antibody will depend, in part, on its ASA specific activity. In some embodiments, the ASA specific activity of a HIR Ab-ASA fusion antibody is at least 10 U/mg of protein, at least about 10, 12, 14, 16, 18, 20, 25, 30, 35, 40, 45, 50, or any other specific activity value from about 10 units/mg to about 50 units/mg.

Thus, with due consideration of the specific activity of a HIR Ab-ASA fusion antibody and the body weight of a subject to be treated, a systemic dose of the HIR Ab-ASA fusion antibody can be at least 5 mg, e.g., 5, 10, 15, 20, 25, 30, 35, 40, 45, 50, 55, 60, 65, 70, 75, 100, 125, or any other value from about 5 mg to about 125 mg of HIR Ab-ASA fusion antibody.

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration. Any suitable HIR Ab-ASA fusion antibody, as described herein, may be used.

An ASA deficiency as referred to herein includes, one or more conditions known as metachromatic leukodystrophy. The ASA deficiency is characterized by the buildup of sulfatides that occurs in the body (the heart, liver, brain etc.).

The compositions of the invention, e.g., an HIR Ab-ASA fusion antibody, may be administered as part of a combination therapy. The combination therapy involves the administration of a composition of the invention in combination with another therapy for treatment or relief of symptoms typically found in a patient suffering from an ASA deficiency. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

In some embodiments, the composition, e.g., an HIR Ab-ASA fusion antibody is co-administered to the patient with another medication, either within the same formulation or as a separate composition. For example, the HIR Ab-ASA fusion antibody may be formulated with another fusion protein that is also designed to deliver across the human blood-brain barrier a recombinant protein other than ASA. Further, the fusion HIR Ab-ASA fusion antibody may be formulated in combination with other large or small molecules.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Expression and Functional Analysis of HIR Ab-GUSB Fusion Protein

The lysosomal enzyme mutated in MPS-VII, also called Sly syndrome, is β-glucuronidase (GUSB). MPS-VII results in accumulation of glycosoaminoglycans in the brain. Enzyme replacement therapy (ERT) of MPS-VII would not likely be effective for treatment of the brain because the GUSB enzyme does not cross the BBB. In an effort to re-engineer human GUSB to cross the BBB, a HIR Ab-GUSB fusion protein project was initiated.

Human GUSB cDNA corresponding to amino acids $Met_1$-$Thr_{651}$ of the human GUSB protein (NP_000172), including the 22 amino acid signal peptide, and the 18 amino acid carboxyl terminal propeptide, was cloned by reverse transcription (RT) polymerase chain reaction (PCR) and custom oligodexoynucleotides (ODNs). PCR products were resolved in 1% agarose gel electrophoresis, and the expected major single band of ~2.0 kb corresponding to the human GUSB cDNA was isolated. The cloned human GUSB was inserted into a eukaryotic expression plasmid, and this GUSB expression plasmid was designated pCD-GUSB. The entire expression cassette of the plasmid was confirmed by bi-directional DNA sequencing. Transfection of COS cells in a 6-well format with the pCD-GSUB resulted in high GUSB enzyme activity in the conditioned medium at 7 days (Table 1, Experiment A), which validated the successful engineering of a functional human GUSB cDNA. The GUSB enzyme activity was determined with a fluorometric assay using 4-methylumbelliferyl beta-L-glucuronide (MUGlcU), which is commercially available. This substrate is hydrolyzed to 4-methylumbelliferone (4-MU) by GUSB, and the 4-MU is detected fluorometrically with a fluorometer using an emission wavelength of 450 nm and an excitation wavelength of 365 nm. A standard curve was constructed with known amounts of 4-MU. The assay was performed at 37 C. with 60 min incubations at pH=4.8, and was terminated by the addition of glycine-carbonate buffer (pH=10.5).

A new pCD-HC-GUSB plasmid expression plasmid was engineered, which expresses the fusion protein wherein the carboxyl terminus of the heavy chain (HC) of the HIR Ab is fused to the amino terminus of human GUSB, minus the 22 amino acid GUSB signal peptide, and minus the 18 amino acid carboxyl terminal GUSB propeptide. The GUSB cDNA was cloned by PCR using the pCD-GUSB as template. The forward PCR primer introduces "CA" nucleotides to maintain the open reading frame and to introduce a Ser-Ser linker between the carboxyl terminus of the CH3 region of the HIR Ab HC and the amino terminus of the GUSB minus the 22 amino acid signal peptide of the enzyme. The GUSB reverse PCR primer introduces a stop codon, "TGA," immediately after the terminal Thr of the mature human GUSB protein. DNA sequencing of the expression cassette of the pCD-HC-GUSB encompassed 4,321 nucleotides (nt), including a 714 nt cytomegalovirus (CMV) promoter, a 9 nt Kozak site (GC-CGCCACC), a 3,228 nt HC-GUSB fusion protein open reading frame, and a 370 nt bovine growth hormone (BGH) transcription termination sequence. The plasmid encoded for a 1,075 amino acid protein, comprised of a 19 amino acid IgG signal peptide, the 443 amino acid HIRMAb HC, a 2 amino acid linker (Ser-Ser), and the 611 amino acid human GUSB minus the enzyme signal peptide and carboxyl terminal propeptide. The GUSB sequence was 100% identical to $Leu^{23}$-$Thr^{633}$ of human GUSB (NP_000172). The predicted molecular weight of the heavy chain fusion protein, minus glycosylation, is 119,306 Da, with a predicted isoelectric point (pI) of 7.83.

COS cells were plated in 6-well cluster dishes, and were dual transfected with pCD-LC and pCD-HC-GUSB, where pCD-LC is the expression plasmid encoding the light chain (LC) of the chimeric HIR Ab. Transfection was performed using Lipofectamine 2000, with a ratio of 1:2.5, ug DNA:uL Lipofectamine 2000, and conditioned serum free medium was collected at 3 and 7 days. However, there was no specific increase in GUSB enzyme activity following dual transfection of COS cells with the pCD-HC-GUSB and pCD-LC expression plasmids (Table 1, Experiment B). However, the low GUSB activity in the medium could be attributed to the low secretion of the HIRMAb-GUSB fusion protein, as the medium IgG was only 23±2 ng/mL, as determined by a human IgG-specific ELISA. Therefore, COS cell transfection was scaled up to 10×T500 plates, and the HIRMAb-GUSB fusion protein was purified by protein A affinity chromatography. IgG Western blotting demonstrated the expected increase in size of the fusion protein heavy chain. However, the GUSB enzyme activity of the HIRMAb-GUSB fusion protein was low at 6.1±0.1 nmol/hr/ug protein. In contrast, the specific activity of human recombinant GUSB is 2,000 nmol/hr/ug protein [Sands et al (1994) Enzyme replacement therapy for murine mucopolysaccharidosis type VII. *J Clin Invest* 93, 2324-2331]. These results demonstrated the GUSB enzyme activity of the HIR Ab-GUSB fusion protein was >95% lost following fusion of the GUSB to the carboxyl terminus of the HC of the HIR Ab. The affinity of HIR Ab-GUSB fusion protein binding to the extracellular domain (ECD) of the HIR was examined with an ELISA. CHO cells permanently transfected with the HIR ECD were grown in serum free media (SFM), and the HIR ECD was purified with a wheat germ agglutinin affinity column. The HIR ECD was plated on 96-well dishes and the binding of the HIR Ab, and the HIR Ab-GUSB fusion protein to the HIR ECD was detected with a biotinylated goat anti-human IgG (H+L) secondary antibody, followed by avidin and biotinylated peroxidase. The concentration of protein that gave 50% maximal binding, $ED_{50}$, was determined with a non-linear regression analysis. The HIR receptor assay showed there was no decrease in affinity for the HIR following fusion of the 611 amino acid GUSB to the carboxyl terminus of the HIRMAb heavy chain. The ED50 of the HIR Ab binding to the HIR ECD was 0.77±0.10 nM and the ED50 of binding of the HIR Ab-GUSB fusion protein was 0.81±0.04 nM.

In summary, fusion of the GUSB to the carboxyl terminus of the HIR Ab HC resulted in no loss in affinity of binding of the fusion protein to the HIR. However, the GUSB enzyme activity of the fusion protein was decreased by >95%.

In an effort to successfully produce a fusion protein of the HIR Ab and GUSB, a new approach was undertaken, in which the carboxyl terminus of the mature human GUSB, including the GUSB signal peptide, was fused to the amino terminus of the HC of the HIR Ab. This fusion protein was designated GUSB-HIR Ab. The first step was to engineer a new expression plasmid encoding this new fusion protein, and this plasmid was designated pCD-GUSB-HC. The pCD-GUSB-HC plasmid expresses the fusion protein wherein the amino terminus of the heavy chain (HC) of the HIRMAb, minus its 19 amino acid signal peptide, is fused to the carboxyl terminus of human GUSB, including the 22 amino acid GUSB signal peptide, but minus the 18 amino acid carboxyl terminal GUSB propeptide. The pCD-GUSB vector was used as template for PCR amplification of the GUSB cDNA expressing a GUSB protein that contained the 22 amino acid GUSB signal peptide, but lacking the 18 amino acid propeptide at the GUSB carboxyl terminus. The GUSB 18 amino acid carboxyl terminal propeptide in pCD-GUSB was deleted by site-directed mutagenesis (SDM). The latter created an AfeI site on the 3'-flanking region of the $Thr^{633}$ residue of GUSB, and it was designated pCD-GUSB-AfeI. The carboxyl terminal propeptide was then deleted with AfeI and HindIII (located on the 3'-non coding region of GUSB). The HIRMAb HC open reading frame, minus the 19 amino acid IgG signal peptide and including the HIRMAb HC stop codon, was generated by PCR using the HIRMAb HC cDNA as template. The PCR generated HIRMAb HC cDNA was inserted at the AfeI-HindIII sites of pCD-GUSB-AfeI to form the pCD-GUSB-HC. A Ser-Ser linker between the carboxyl terminus of GUSB and amino terminus of the HIRMAb HC was introduced within the AfeI site by the PCR primer used for the cloning of the HIRMAb HC cDNA. DNA sequencing of the pCD-GUSB-HC expression cassette showed the plasmid expressed 1,078 amino acid protein, comprised of a 22 amino acid GUSB signal peptide, the 611 amino acid GUSB, a 2 amino acid linker (Ser-Ser), and the 443 amino acid HIRMAb HC. The GUSB sequence was 100% identical to $Met^1$-$Thr^{633}$ of human GUSB (NP_000172).

Dual transfection of COS cells in a 6-well format with the pCD-LC and pCD-GUSB-HC expression plasmids resulted in higher GUSB enzyme activity in the conditioned medium at 7 days, as compared to dual transfection with the pCD-LC and pCD-HC-GUSB plasmids (Table 1, Experiment C). However, the GUSB-HIRMAb fusion protein was also secreted poorly by the COS cells, as the medium human IgG concentration in the 7 day conditioned medium was only 13±2 ng/mL, as determined by ELISA. COS cell transfection was scaled up to 10×T500 plates, and the GUSB-HIRMAb fusion protein was purified by protein A affinity chromatography. SDS-PAGE demonstrated the expected increase in size of the fusion protein heavy chain. The GUSB enzyme activity of the purified GUSB-HIRMAb fusion protein was high at 226±8 nmol/hr/ug protein, which is 37-fold higher than the specific GUSB enzyme activity of the HIRMAb-GUSB fusion protein. However, the HIR receptor assay showed there was a marked decrease in affinity for the HIR following fusion of the GUSB to the amino terminus of the HIRMAb heavy chain, which resulted in a 95% reduction in receptor binding affinity. The ED50 of the HIR Ab binding to the HIR ECD was 0.25±0.03 nM and the ED50 of binding of the HIR Ab-GUSB fusion protein was 4.8±0.4 nM.

In summary, fusion of the GUSB to the amino terminus of the HIR Ab HC resulted in retention of GUSB enzyme activity of the fusion protein, but caused a 95% reduction in binding of the GUSB-HIR Ab fusion protein to the HIR. In contrast, fusion of the GUSB to the carboxyl terminus of the HIR Ab HC resulted in no loss in affinity of binding of the HIR Ab-GUSB fusion protein to the HIR. However, the GUSB enzyme activity of this fusion protein was decreased by >95%. These findings illustrate the unpredictable nature of the art of fusion of lysosomal enzymes to IgG molecules in such a way that bi-functionality of the IgG-enzyme fusion protein is retained, i.e., high affinity binding of the IgG part to the cognate antigen, as well as high enzyme activity.

TABLE 1

GUSB enzyme activity in COS cells following transfection
[Mean ± SE (n = 3 dishes per point)]

| Experiment | Treatment | Medium GUSB activity (nmol/hour/mL) |
|---|---|---|
| A | Lipofectamine 2000 | 65 ± 1 |
|   | pCD-GUSB | 6892 ± 631 |
| B | Lipofectamine 2000 | 76 ± 3 |
|   | pCD-HC-GUSB, pCD-LC | 72 ± 3 |
| C | Lipofectamine 2000 | 162 ± 7 |
|   | pCD-HC-GUSB, pCD-LC | 155 ± 2 |
|   | pCD-GUSB-HC, pCD-LC | 1119 ± 54 |

Example 2

Figure 2:
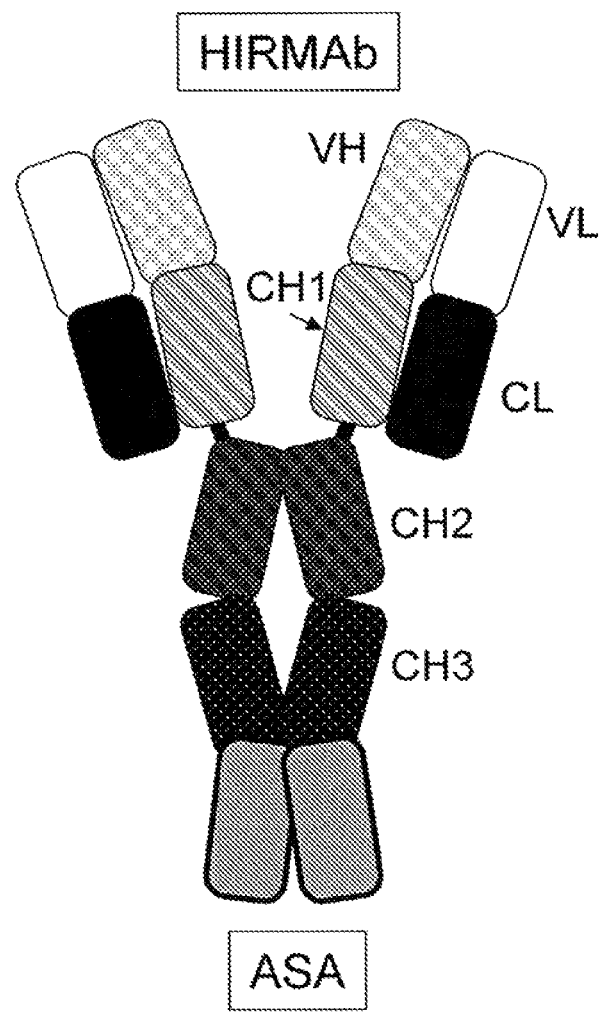
FIG. 2. An exemplary HIR Ab-ASA fusion antibody is formed by fusion of the amino terminus of the mature ASA to the carboxyl terminus of the CH3 region of the heavy chain of the HIR Ab.
Figure 3:
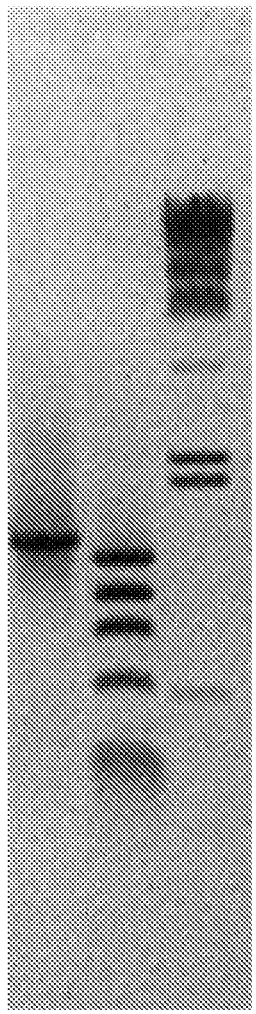
FIG. 3. Ethidium bromide stain of agarose gel of human ASA cDNA (left lane), which was produced by PCR from human liver cDNA, and ASA-specific primers (Table 2). Middle and right lanes: PhiX174 HaeIII digested DNA standard, and Lambda HindIII digested DNA standard.

Construction of Human HIR Ab Heavy Chain-ASA Fusion Protein Expression Vector The lysosomal enzyme mutated in metachromatic leukodystrophy (MLD) is arysulfatase A (ASA). MLD results in accumulation of sulfatides in the brain, particularly in the myelin sheath. Enzyme replacement therapy of MLD would likely not be effective for treatment of the brain because the ASA enzyme does not cross the BBB. ASA was fused to the HIR Ab in order to develop a bifunctional molecule capable of both crossing the BBB and exhibiting enzymatic activity. In one embodiment the amino terminus of the mature ASA is fused to the carboxyl terminus of each heavy chain of the HIR Ab (FIG. 2).

It was unclear whether the enzymatic activity of the ASA would be retained when it was fused to the HIR Ab. The experience with IgG-GUSB fusion proteins described above illustrates the unpredictable nature of the art, and the chance that either the IgG part or the lysosomal enzyme part could lose biological activity following construction of the IgG-enzyme fusion protein. The situation with ASA is even more complex, since the ASA enzyme does become catalytically active until there is a post-translational modification of the protein, wherein the Cys residue near the amino terminus (Cys-515 of SEQ ID NO 10) undergoes a post-translational modification within the endoplasmic reticulum, and it was not known whether that process would be compromised when ASA was fused to HIR Ab. ASA is a member of a family of sulfatases, wherein the activity of the enzyme is activated following the conversion of a specific Cys residue to a formylglycine residue by a sulfatase modifying factor type 1 (SUMF1), also called formylglycine-generating enzyme (FGE), in the endoplasmic reticulum [Takakusaki et al, Coexpression of formylglycine-generating enzyme is essential for synthesis and secretion of functional arylsulfatase A in a mouse model of metachromatic leukodystrophy. *Human Gene Ther.* 16 (2005) 929-936]. Without this conversion of the internal cysteine into a formylglycine residue, the enzyme has no activity. If the ASA was fused to the carboxyl terminus of the HC of the HIR Ab, e.g. in an effort to retain high affinity binding of the fusion protein to the HIR, then the IgG heavy chain would fold into the 3-dimensional structure following translation within the host cell, followed by folding of the ASA part of the fusion protein. It was uncertain as to whether the ASA part of the HIR Ab HC-ASA fusion protein would fold into a 3-dimensional structure that would be recognized by, and activated by, the ASA-modifying factors in the endoplasmic reticulum, resulting in expression of full ASAenzyme activity in the HIR Ab-ASA fusion protein.

The cDNA for the human arylsulfatase A (ARSA) was produced by the polymerase chain reaction (PCR) using oligodeoxynucleotides (ODN) derived from the nucleotide sequence of the human ASA mRNA (GenBank accession #NM_000487). The cDNA encoding human ASA, minus its signal peptide, Arg19-Ala-507, was generated by reverse transcription (RT) PCR using the ODNs described in Table 2, and commercially available human liver PolyA+ RNA. The forward (FOR) ODN primer has "CC" on the 5'-flanking region to maintain the open reading frame (orf) with the CH3 region of human IgG1 in the TV expression vector and to introduce a Ser-Ser linker between the human IgG1-CH3 and ASA cDNA. The reverse (REV) ODN is complementary to the end of ASA orf and includes its stop codon, TGA. RT-PCR was completed and the expected single band of ~1.5 kb corresponding to ASA orf cDNA was detected by agarose gel electrophoresis (FIG. 3, lane 1) and gel purified. Both forward and reverse ODNs are phosphorylated for direct insertion into the expression vector. The ASA cDNA was inserted into at the HpaI site of a precursor TV, pUTV-1, with T4 DNA ligase to form TV-HIRMAb-ASA, which is outlined in FIG. 4. The pUTV-1 was linearized with HpaI and digested with alkaline phosphatase to prevent self ligation. The TV-HIRMAb-ASA is a tandem vector that encompasses the genes for both the light chain (LC) and heavy chain (HC), respectively, of the HIRMAb-ASA fusion protein followed by the murine dihydrofolate reductase (DHFR) gene. The genes for the light and heavy chain of the HIRMAb-ASA fusion protein are driven by the CMV promoter and the orfs are followed by the bovine growth hormone (BGH) polyadenylation sequence. The DHFR gene is under the influence of the SV40 promoter and contains the hepatitis B virus (HBV) polyadenylation termination sequence. The DNA sequence of the TV-HIRMAb-ASA plasmids was confirmed by bi-directional DNA sequencing performed at MWG Biotech, Inc. (Huntsville, Ala.) using custom ODNs synthesized at Midland (Midland, Tex.). The fusion of the ASA monomer to the carboxyl terminus of each HC is depicted in FIG. 2. The entire expression cassette of the plasmid was confirmed by sequencing both strands.

TABLE 2

Oligodeoxynucleotide primers used in the RT-PCR cloning of human arylsulfatase A (ASA) minus signal peptide and in the engineering of the HIRMAb-ASA expression vector, derived from human ASA mRNA sequence (GenBank NM_000487).

| | |
|---|---|
| ASA FWD: | phosphate-CCCGTCCGCCCAACATCGTGCT (SEQ ID NO. 11) |
| ASA REV: | phosphate-TCAGGCATGGGGATCTGGGCAATG (SEQ ID NO. 12) |

DNA sequencing of the TV-HIRMAb-ASA plasmid encompassed 9,999 nucleotides (nt), which covered the expression cassettes for the LC gene, the HC-ASA gene, and the DHFR gene (FIG. 4). Beginning at the 5'-end, the plasmid was comprised of a cytomegalovirus (CMV) promoter, a 9 nt full Kozak site, GCCGCCACC (nt 1-9 of SEQ ID NO: 13), a 705 nt open reading frame (orf) for the LC (nt 10-714 of SEQ ID NO: 13), followed by a bovine growth hormone (BGH) polyA sequence, followed by a linker sequence, followed by a tandem CMV promoter, followed by a full Kozak site (nt 1-9 of SEQ ID NO: 14), followed by a 2,862 nt HIRMAb HC-ASA fusion protein orf (nt 10-2871 of SEQ ID NO: 14), followed by a tandem BGH poly A sequence, followed by the SV40 promoter, followed by a full Kozak site (nt 1-9 of SEQ ID NO: 15), followed by the 564 nt of the DHFR orf (nt 10-573 of SEQ ID NO: 15), followed by the hepatitis B virus poly A sequence (FIG. 4). The TV encoded for a 214 amino acid HIRMAb LC (SEQ ID NO: 8), which included a 20 amino acid signal peptide; a 953 amino acid protein fusion protein of the HIRMAb HC and ASA (SEQ ID NO:10). The fusion protein HC was comprised of a 19 amino acid IgG signal peptide, the 442 amino acid HIRMAb HC, a 3 amino acid linker (Ser-Ser-Ser), and the 489 amino acid human ASA minus the enzyme signal peptide. The predicted molecular weight of the heavy chain fusion protein, minus glycosylation, is 100,637 Da, with a predicted isoelectric point (pI) of 6.43. The amino acid sequence of the ASA domain of the HC fusion protein is 100% identical to the sequence of amino acids 21-509 of human ASA (NP_000478), with the exception of the T391S polymorphism within the ASA domain of the fusion protein. This residue is frequently a threonine (T or Thr) residue, but is also known to be a serine (S or Ser) residue. The T391S polymorphism has no effect on the enzyme activity of ASA (S. Regis et al, Contribution of arylsulfatase A mutations located on the same allele to enzyme activity reduction and metachromatic leukodystrophy severity, Hum. Genet. 110: 351-355, 2002).

Example 3

Stable Transfection of Chinese Hamster Ovary Cells with TV-HIRMAb-ASA

Chinese hamster ovary (CHO) cells were grown in serum free HyQ SFM4-CHO utility medium (HyClone), containing 1×HT supplement (hypoxanthine and thymidine). CHO cells ($5×10^6$ viable cells) were electroporated with 5 µg PvuI-linearized TV-HIRMAb-ASA plasmid DNA. The cell-DNA suspension was then incubated for 10 min on ice. Cells were electroporated with BioRad pre-set protocol for CHO cells, i.e. square wave with pulse of 15 msec and 160 volts. After electroporation, cells were incubated for 10 min on ice. The cell suspension was transferred to 50 ml culture medium and plated at 125 µl per well in 4×96-well plates (10,000 cells per well). A total of 10 electroporations and 4,000 wells were performed per study.

Figure 4:
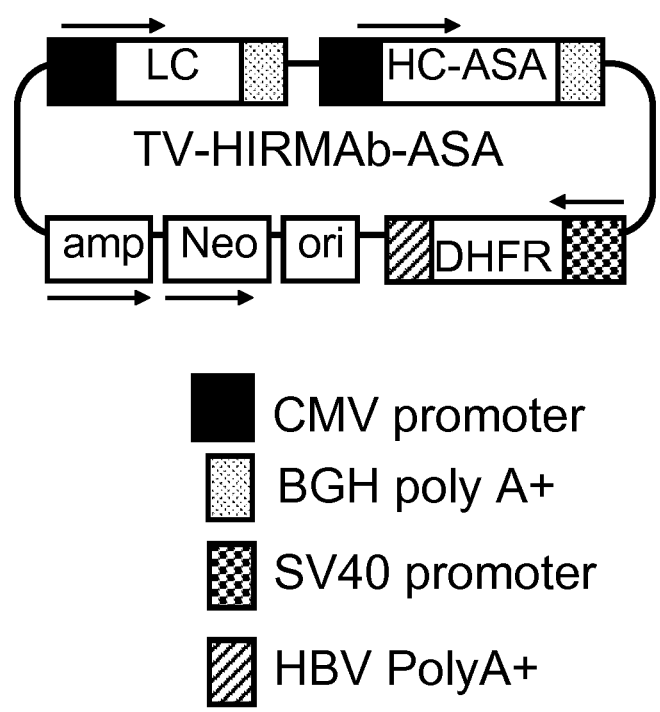
FIG. 4. Genetically engineered tandem vector (TV-HIRMAb-ASA) encoding 4 separate and tandem expression cassettes encoding the heavy chain (HC) fusion gene, the light chain (LC) gene, the DHFR gene, and the neo gene.

Following electroporation (EP), the CHO cells were placed in the incubator at 37 C. and 8% CO2. Owing to the presence of the neo gene in the TV, transfected cell lines were initially selected with G418. The TV-HIRMAb-ASA also contains the gene for DHFR (FIG. 4), so the transfected cells were also selected with 20 nM methotrexate (MTX) and HT deficient medium. Once visible colonies were detected at about 21 days after EP, the conditioned medium was sampled for human IgG by ELISA. Wells with high human IgG signals in the ELISA were transferred from the 96-well plate to a 24-well plate with 1 mL of HyQ SFM4-CHO-Utility. The 24-well plates were returned to the incubator at 37 C. and 8% CO2. The following week IgG ELISA was performed on the clones in the 24-well plates. This was repeated through the 6-well plates to T75 flasks and finally to 60 ml- and 125 mL square plastic bottles on an orbital shaker. At this stage, the final MTX concentration was 80 nM, and the medium IgG concentration, which was a measure of HIRMAb-ASA fusion protein in the medium is >10 mg/L at a cell density of $10^6$/mL.

Clones selected for dilutional cloning (DC) were removed from the orbital shaker in the incubator and transferred to the sterile hood. The cells were diluted to 500 mL in F-12K medium with 5% dialyzed fetal bovine serum (d-FBS) and Penicillin/Streptomycin, and the final dilution is 8 cells per mL, so that 4,000 wells in 40×96-well plates can be plated at a cell density of 1 cell per well (CPW). Once the cell suspension was prepared, within the sterile hood, a 125 uL aliquot was dispensed into each well of a 96-well plate using an 8-channel pipettor or a precision pipettor system. The plates were returned to the incubator at 37 C. and 8% CO2. The cells diluted to 1 cell/well cannot survive without serum. On day 6 or 7, DC plates were removed from the incubator and transferred to the sterile hood where 125 µl of F-12K medium with 5% dialyzed fetal bovine serum (d-FBS) was added to each well. This selection media now contained 5% d-FBS, 30 nM MTX and 0.25 mg/mL Geneticin. On day 21 after the initial 1 CPW plating, aliquots from each of the 4,000 wells were removed for human IgG ELISA, using robotics equipment. DC plates were removed from the incubator and transferred to the sterile hood, where 100 µl of media was removed per well of the 96-well plate and transferred into a new, sterile sample 96-well plate using an 8-channel pipettor or the precision pipettor system.

On day 20 after the initial 1 CPW plating, 40×96-well Immunoassay plates were plated with 100 uL of 1 µg/mL solution of Primary antibody, a mouse anti-human IgG in 0.1M NaHCO3. Plates are incubated overnight in the 4 C. refrigerator. The following day, the ELISA plates were washed with 1×TBST 5 times, and 100 uL of 1 ug/mL solution of secondary antibody and blocking buffer were added. Plates are washed with 1×TBST 5 times. 100 uL of 1 mg/mL of 4-nitrophenyl phosphate di(2-amino-2-ethyl-1,3-propanediol) salt in 0.1 M glycine buffer are added to the 96-well immunoassay plates. Plates were read on a microplate reader. The assay produced IgG output data for 4,000 wells/experiment. The highest producing 24-48 wells were selected for further propagation.

The highest producing 24-well plates from the 1 CPW DC were transferred to the sterile hood and gradually subcloned through 6-well dishes, T75 flasks, and 125 mL square plastic bottles on an orbital shaker. During this process the serum was reduced to zero, at the final stage of centrifugation of the cells and resuspension in SFM.

The above procedures were repeated with a second round of dilutional cloning, at 0.5-1 cells/well (CPW). At this stage, approximately 40% of the wells showed any cell growth, and all wells showing growth also secreted human IgG. These results confirmed that on average only 1 cell is plated per well with these procedures, and that the CHO cell line originates from a single cell.

The HIR Ab-ASA fusion protein was secreted to the medium by the stably transfected CHO cells in high amounts at medium concentrations of 10-20 mg/L at a cell density of 1-2 million cells/mL. The high production of the HIR Ab-ASA fusion protein by the stably transfected CHO cells was observed, even though there was no dual transfection of the host cell with the fusion protein genes and the gene encoding SUMF1. In cells transfected with the ASA gene, it was necessary to co-transfect with the SUMF1 co-factor in order to detect secretion of the ASA to the medium conditioned by the transfected host cell [Takakusaki et al, Coexpression of formylglycine-generating enzyme is essential for synthesis and secretion of functional arylsulfatase A in a mouse model of metachromatic leukodystrophy. *Human Gene Ther.* 16 (2005) 929-936]. An unexpected advantage of engineering ASA and an IgG-ASA fusion protein is that the host cell secretes the fusion protein without the requirement for the co-transfection with SUMF1.

Figure 10:
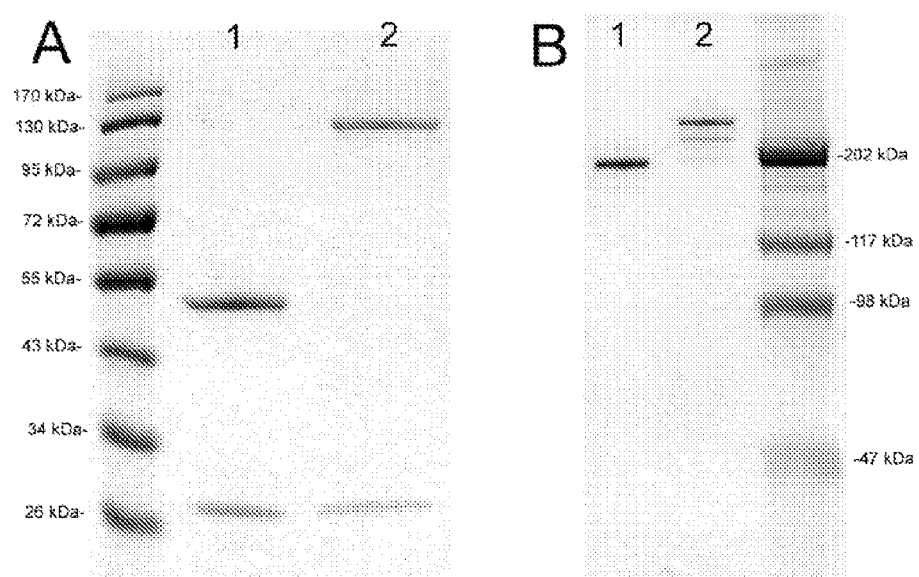
FIG. 10. SDS-PAGE of molecular weight standards, the purified HIRMAb (lane 1), and the purified HIRMAb-ASA fusion protein (lane 2). (A) Reducing SDS-PAGE gel. (B) Non-reducing SDS-PAGE gel.
Figure 11:
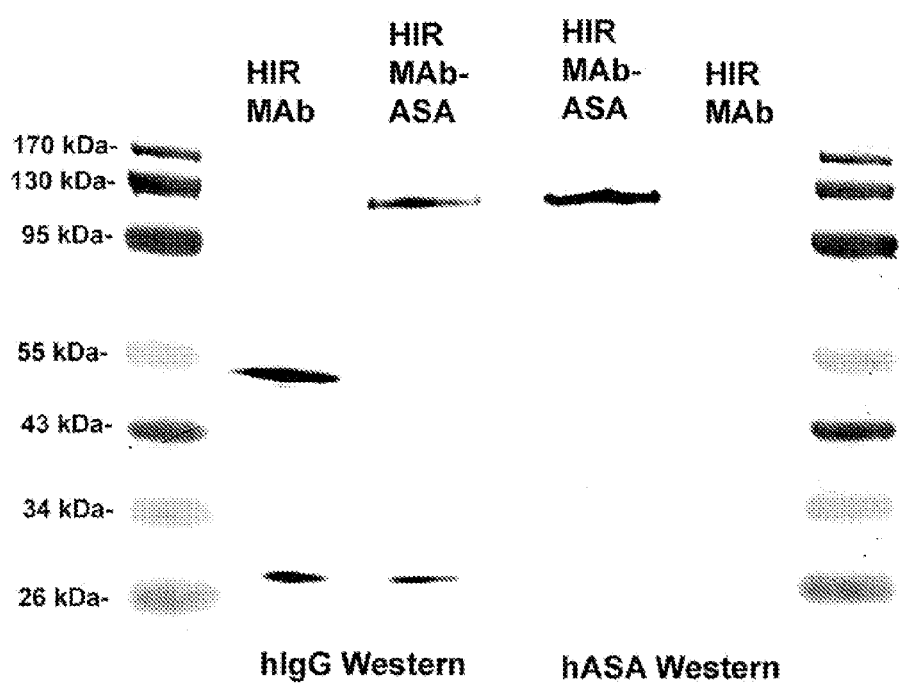
FIG. 11. Western blot with either anti-human (h) IgG primary antibody (left panel) or anti-human ASA primary antiserum (right panel). The immunoreactivity of the HIRMAb-ASA fusion protein is compared to the chimeric HIRMAb. Both the HIRMAb-ASA fusion protein and the HIRMAb have identical light chains on the anti-hIgG Western. The HIRMAb-ASA fusion heavy chain reacts with both the anti-hIgG and the anti-human ASA antibody, whereas the HIRMAb heavy chain only reacts with the anti-hIgG antibody.

The CHO-derived HIRMAb-ASA fusion protein was purified by protein A affinity chromatography. The purity of the HIRMAb-ASA fusion protein was verified by reducing and non-reducing SDS-PAGE as shown in FIGS. 10A and 10B, respectively. Only the HC and LC proteins are detected for either the HIRMAb alone or the HIRMAb-ASA fusion protein. The identity of the fusion protein was verified by Western blotting using primary antibodies to either human IgG (FIG. 11, left panel) or human ASA (FIG. 11, right panel). The molecular weight (MW) of the HIRMAb-ASA heavy and light chains, and the MW of the HIRMAb heavy and light chains are estimated by linear regression based on the migration of the MW standards. The size of the HIRMAb-ASA fusion heavy chain, 119 kDa, is 61 kDa larger than the size of the heavy chain of the HIRMAb, 58 kDa, owing to the fusion of the ASA to the 58 kDa HIRMAb heavy chain. The size of the light chain, 25 kDa, is identical for both the HIRMAb-ASA fusion protein and the HIRMAb antibody, as both proteins use the same light chain. The estimated MW of the hetero-tetrameric HIRMAb-ASA fusion protein shown in FIG. 2 is 288 kDa, based on migration in the SDS-PAGE of the Western blot.

Example 4

Figure 12:
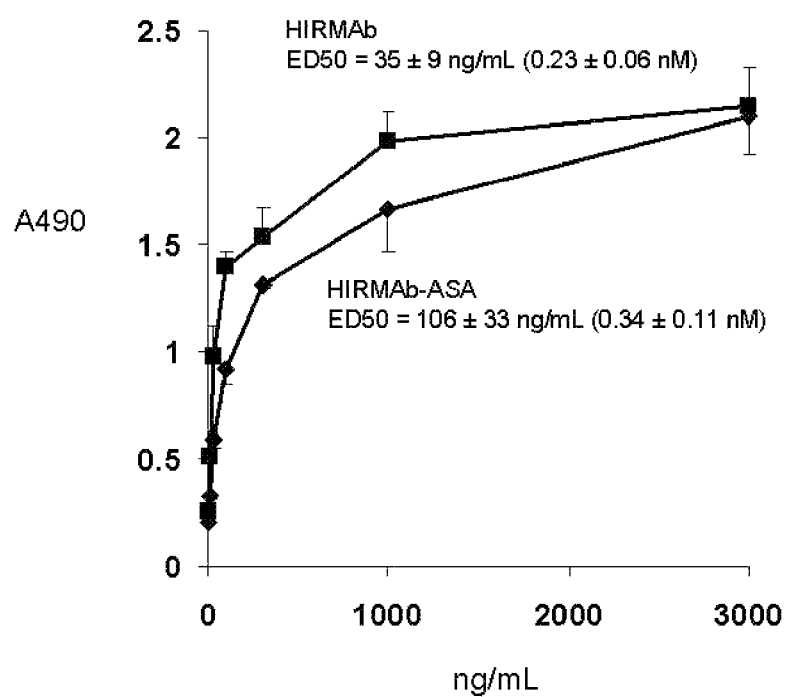
FIG. 12. Binding of either the chimeric HIRMAb or the HIRMAb-ASA fusion protein to the HIR extracellular domain (ECD) is saturable. The $ED_{50}$ of HIRMAb-ASA binding to the HIR ECD is comparable to the $ED_{50}$ of the binding of the chimeric HIRMAb, after normalization for differences in molecular weight.

Analysis of HIR Binding and ASA Activity of the Bi-Functional IgG-ASA Fusion Protein The affinity of the fusion protein for the HIR extracellular domain (ECD) was determined with an ELISA. CHO cells permanently transfected with the HIR ECD were grown in serum free media (SFM), and the HIR ECD was purified with a wheat germ agglutinin affinity column, as previously described in Coloma et al. (2000) *Pharm Res,* 17:266-274. The HIR ECD was plated on Nunc-Maxisorb 96 well dishes and the binding of the HIR Ab, or the HIR Ab-ASA fusion protein, to the HIR ECD was detected with a biotinylated goat anti-human IgG (H+L) secondary antibody, followed by avidin and biotinylated peroxidase (Vector Labs, Burlingame, Calif.). The concentration of either HIR Ab or HIR Ab-ASA fusion protein that gave 50% maximal binding, ED50, was determined with a non-linear regression analysis. The ED50 of binding to the HIR is 35±9 ng/mL and the ED50 of binding to the HIR of the HIR Ab-ASA fusion protein is 106±33 ng/mL (FIG. 12). The MW of the HIR Ab is 150 kDa, and the MW of the HIR Ab-ASA fusion protein is 288 kDa. Therefore, after normalization for MW differences, there was comparable binding of either the chimeric HIR Ab or the HIR Ab-ASA fusion protein for the HIR ECD with ED50 of 0.23±0.06 nM and 0.34±0.11 nM, respectively (FIG. 12). These findings show that the affinity of the HIR Ab-ASA fusion protein binding to the HIR is retained, despite fusion of a ASA molecule to the carboxyl termini of both heavy chains of the IgG.

Figure 13:
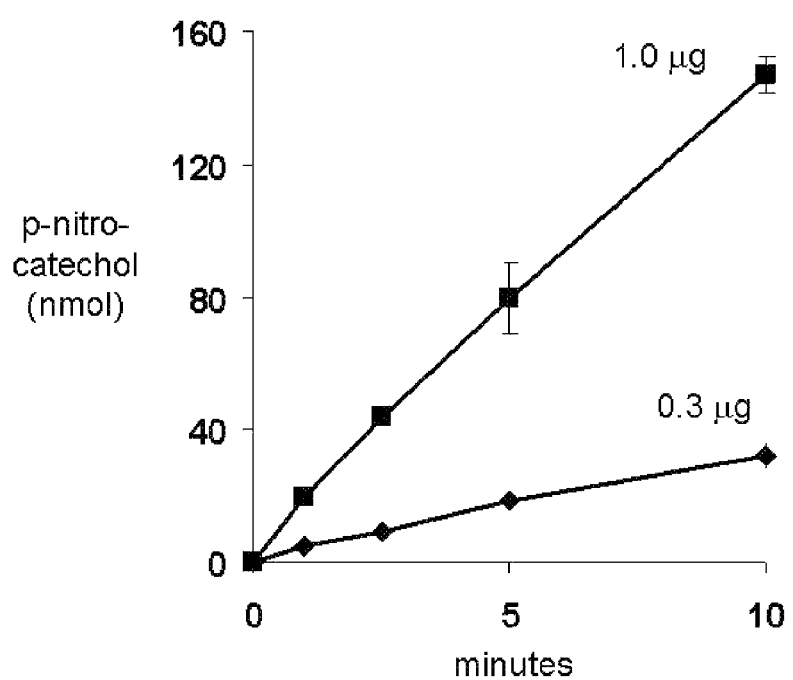
FIG. 13. Spectrophotometric assay using para-nitrocatechol sulfate (NCS) as the substrate is used to quantify the ASA specific activity of the HIRMAb-ASA fusion protein at 2 doses of the fusion protein (0.3 and 1.0 ug). The assay is linear through 10 minutes of the reaction.

The ASA enzyme activity was determined with a spectrophotometric assay using p-nitrocatechol sulfate (NCS), which is available from the Sigma Co (St Louis, Mo.). This substrate is hydrolyzed by ASA to p-nitrocatechol (NC), which is detected spectrophotometrically at 515 nm. A standard curve was constructed with known amounts of NC (Sigma). The assay was performed by incubation at 37 C. at pH=5.0 for 10 minutes in 0.25 M sodium acetate/1 M NaCl/0.25 mM sodium pyrophosphate/0.1% bovine serum albumin The incubation was terminated by the addition of 0.2 mL of 1 M NaOH. One unit=1 umol/min. The enzyme activity was linear with respect to time and mass of fusion protein (FIG. 13), and the average enzyme activity was 20±1 umol/min/mg protein, or 20 units/mg protein. The ASA enzyme specific activity of recombinant human ASA, using the same assay, is 60 units/mg protein [Matzner et al (2008): Non-inhibitory antibodies impede lysosomal storage reduction during enzyme replacement therapy of a lysosomal storage disease. J. Mol. Med. 86: 433-442]. However, following re-engineering of the ASA as an IgG-ASA fusion protein, the effective MW of the ASA is 144 kDa, whereas the MW of ASA is 60 kDa. Therefore, after normalization for MW differences, the effective ASA specific activity is 50 units/mg protein, which is comparable to recombinant ASA. Therefore, fusion of the ASA to the carboxyl terminus of the HC of the HIR Ab had minimal effect on the enzyme activity of the ASA enzyme, in contrast to the result observed with the IgG-GUSB fusion protein (Table 1). The high ASA enzyme activity of the CHO-derived HIR Ab-ASA fusion protein is surprising, because ASA is a member of a family of sulfatases that requires a specific post-translational modification for expression of ASA enzyme activity. The activity of the ASA enzyme is activated following the conversion of Cys-59 to a formylglycine residue by a sulfatase modifying factor type 1 (SUMF1), which is also called the formylglycine generating enzyme (FGE). The retention of ASA enzyme activity in the HIRMAb-ASA fusion protein produced by the stably transfected CHO cells indicates the ASA enzyme is activated within the host cell despite fusion to the HIRMAb heavy chain.

Example 5

Amino Acid Linker Joining the ASA and the Targeting Antibody

The mature human ASA is fused to the carboxyl terminus of the HC of the HIR Ab with a 3-amino acid linker, Ser-Ser-Ser (underlined in FIG. 9). Any number of variations of linkers are used as substitutions for the Ser-Ser-Ser linker. The 3-amino acid linker may be retained, but the amino acid sequence is changed to alternative amino acids, such as Gly-Gly-Gly, or Ser-Gly-Ser, or Ala-Ser-Gly, or any number of combinations of the 20 natural amino acids. Or, the linker is reduced to a two, one or zero amino acids. In the case of a zero amino acid linker, the amino terminus of the ASA is fused directly to the carboxyl terminus of the HC of the HIR Ab. Alternatively, the length of the linker is expanded to 3, 4, 5, 6, 7, 8, 9, 10, 11, 12, 13, 14, 15, or 20 amino acids. Such linkers are well known in the art, as there are multiple publicly available programs for determining optimal amino acid linkers in the engineering of fusion proteins. A frequently used linker includes various combinations of Gly and Ser in repeating sequences, such as $(Gly_4Ser)_3$, or other variations Example 6

HIR Ab-ASA Fusion Protein Uptake and Biological Activity in MLD Fibroblasts

MLD fibroblasts were obtained from the Coriell Institute for Medical Research (Camden, N.J.), and grown overnight in DMEM with 10% FBS to >50% confluency in Lab-Tek chamber slide plates. The medium was aspirated, the wells washed well with PBS, and the cells were treated with fresh DMEM with no serum and containing 10 ug/mL of the HIRMAb-ASA fusion protein. Following a 24 hr incubation at 37 C., the medium was aspirated, the wells washed extensively with cold PBS, and the cells were fixed with 100% cold methanol for 20 min at −20° C. Following a PBS wash, the plates were blocked with 10% donkey serum, and then co-labeled with 10 ug/mL of a goat anti-ASA antibody, and 10 ug/ml of a mouse MAb to human lysosomal associated membrane protein (LAMP)-1. Negative control antibodies were the same concentrations of either goat or mouse IgG. The secondary antibodies were 5 ug/mL each of Alexa Fluor-488 conjugated donkey anti-mouse IgG (green channel) and Alexa Fluor-594 conjugated donkey anti-goat IgG (red channel). The washed slides were mounted with Vectashield mounting medium containing 4',6-diamidino-2-phenylindole (DAPI). Confocal microscopy was performed with a Leica TCS SP2 AOBS inverted fluorescence microscope. Optical sections (1 um, resolution 300 nm) were obtained sequentially through the z-plane of each sample. The LAMP1 immunoreactivity within the cell is detected in the green channel, and the ASA immunoreactivity is detected in the red channel. There is abundant ASA immunoreactivity within the MLD fibroblast indicating the target cell takes up the HIRMAb-ASA fusion protein. The overlap of the ASA and LAMP1 immunoreactivity is observed, which means the HIRMAb-ASA fusion protein is triaged to the lysosomal compartment of the cell. There is no immunoreactivity in the cells labeled with the isotype control antibodies, which shows the intracellular LAMP1 and ASA immunoreactivity is specific for the targeted protein.

The intracellular ASA immunoreactivity detected with confocal microscopy represents the intact HIRMAb-ASA fusion protein. This was demonstrated with a Western blotting method. Following incubation of the MLD fibroblasts with the HIRMAb-ASA fusion protein for 4 hours, the medium was removed and the cells were washed extensively to remove extracellular fusion protein. The cells were lysed with sodium dodecyl sulfate (SDS) sample buffer and the cell extract was analysed with the Western blot method using a primary antibody against human ASA. Similar to the heavy chain fusion protein shown in FIG. 11 (right panel), the heavy chain of the HIRMAb-ASA fusion protein was detected in the MLD fibroblasts.

Example 7

Receptor-Mediated Delivery of ASA to the Human Brain

Metachromatic leukodystrophy, or MLD, is a lysosomal storage disorder caused by defects in the gene encoding the lysosomal enzyme, arylsulfatase A (ASA). In the absence of ASA, certain sulfoglycolipids accumulate in the cells of the brain, including oliogodendrocytes, neurons, and astrocytes (Eckhardt M., The role and metabolism of sulfatide in the nervous system, Mol Neurobiol, 37: 93-103, 2008). The accumulation of the sulfatide glycolipids in the brain leads to the clinical manifestations of MLD, which includes gait disturbances and ataxia, spastic quadriplegia, seizures, and eventually death in a decerebrated state. The nucleotide sequence of the ASA mRNA and the amino acid sequence of the human ASA protein is known (C. Stein et al, Cloning and expression of human arylsulfatase A, J. Biol. Chem. 264: 1252-1259, 1989). This sequence enables the production of recombinant ASA for the enzyme replacement therapy (ERT) of MLD. ASA produced in Chinese hamster ovary has a specific activity of 60 units/mg enzyme (U. Matzner et al, Enzyme replacement improves nervous system pathology and function in a mouse model for metachromatic leukodystrophy, Human Mol. Genet., 14: 1139-1152, 2005). The ASA specific activity is determined by the p-nitrocatechol sulfate (NCS) spectrophotometric assay (H. Baum et al, The assay of arylsulphatase A and B in human urine, Clin. Chim. Acta 4: 453-455, 1959), where 1 unit=1 umol/min (E. Shapira and H. L. Nadler, Purification and some properties of soluble human liver arylsulfatases, Arch. Biochem. Biophys., 170: 179-187, 1975). The problem with ERT of MLD with recombinant ASA, with respect to treatment of the severe neuropathology of the brain, is that ASA, like other large molecule pharmaceuticals, does not cross the BBB. The administration of a large dose, 40 mg/kg, IV to the MLD mouse does not result in the increase in the immunoreactive ASA in the mouse brain, and does not result in the decrease in the sulfatide content in brain in the MLD mouse (U. Matzner et al, Enzyme replacement improves nervous system pathology and function in a mouse model for metachromatic leukodystrophy, Human Mol. Genet., 14: 1139-1152, 2005). Owing to the lack of transport of ASA across the BBB, it is not possible to increase ASA in brain following the systemic injection of large doses of the enzyme. Accordingly, ERT in MLD patients with recombinant ASA was found to have no beneficial effect on the brain (C. i. Dali and A. M. Lund, Intravenous enzyme replacement therapy for metachromatic leukodystrophy (MLD), Abstracts of American College Medical Genetics Annual Meeting, abstract No. 195, 2009. In an attempt to by-pass the BBB by the direct intra-cerebroventricular (ICV) infusion of ASA into the brains of MLD mice, the enzyme was infused into the ventricle over 4 weeks (S. Stroobants et al, Intracerebroventricular enzyme infusion corrects central nervous system pathology and dysfunction in a mouse model of metachromatic leukodystrophy, Human Molec. Genet., 20: 2760-2769, 2011). The tissue half-life of ASA in brain was <10 minutes following the ICV infusion, whereas the tissue half-life of ASA in peripheral tissues following IV administration is 4 days (U. Matzner et al, Enzyme replacement improves nervous system pathology and function in a mouse model for metachromatic leukodystrophy, Human Mol. Genet., 14: 1139-1152, 2005). The rapid efflux of ASA from brain following ICV infusion is expected, since an ICV injection is like a slow intravenous injection, owing to rapid movement of the drug from the ventricular compartment to the peripheral venous circulation. Nevertheless, ASA infusion into the brain was observed to correct lysosomal storage disease in the MLD mouse.

Example 8

Receptor-Mediated Delivery of ASA to the Monkey Brain

The treatment of patients with MLD, particularly infants with chronic ICV infusion of recombinant ASA, is problematic owing to the requirement of a neurosurgical intervention with placement of intra-cerebral cannulas. However, the more important limitation with the ICV infusion delivery is the limited penetration of the enzyme into brain parenchyma following ICV injection. Owing to the rapid movement of the enzyme from the ventricle space to the peripheral blood, there is limited diffusion of the enzyme into brain tissue beyond that which is in contact with the ependymal surface of the brain. A preferred approach to the delivery of ASA to the brain of MLD patients is via an intravenous infusion of a form of ASA that is re-engineered to cross the BBB via receptor-mediated transport (RMT). The HIRMAb-ASA fusion protein retains high affinity binding to the human insulin receptor, which enables the sulfatase to penetrate the BBB and enter brain from blood via RMT on the endogenous BBB insulin receptor. The brain uptake of the HIRMAb-sulfatase fusion protein is 1.1% of injected dose (ID) per 100 grams brain in the Rhesus monkey, as discussed below. Given this level of brain uptake of the fusion protein, the intravenous administration of 2.5 mg/kg of the IgG-ASA fusion protein, in a 50 kg human, will result in a brain concentration of 1,375 ug of fusion protein/brain. Since the ASA constitutes about half of the fusion protein, the brain concentration of the ASA enzyme is 687 ug/brain, which is equivalent to 687 ng/gram, since the brain of a human weighs about 1000 grams, and is equivalent to 6.9 ng/mg brain protein, since 1 gram of brain contains 100 mg protein. This level of brain uptake of exogenous ASA restores >6% of the normal concentration of ASA in the human brain, since the concentration of immunoreactive ASA in human brain is 100 ng/mg protein (C. Sevin et al, Intracerebral adeno-associated virus-mediated gene transfer in rapidly progressive forms of metachromatic leukodystrophy, Human Molec. Genet., 15: 53-64, 2006). Enzyme replacement therapy in patients with lysosomal storage disorders that produces a cellular enzyme activity of just 1-2% of normal do not develop signs and symptoms of the disease (J.

Muenzer and A. Fisher, Advances in the treatment of mucopolysaccharidosis type I, N. Engl J Med, 350: 1932-1934, 2004). With respect to MLD, there are patients with ASA pseudo-deficiency, which is about 7% of the population, who are clinically normal but have as little as 3% of the normal ASA enzyme activity (Penzien J M, et al. (1993) Compound heterozygosity for metachromatic leukodystrophy and arylsulfatase A pseudodeficiency alleles is not associated with progressive neurological disease. *Am J Hum Genet* 52:557-564). These considerations show that a clinically significant ASA enzyme replacement of the human brain is possible following the intravenous infusion of the HIRMAb-ASA fusion protein at a systemic dose, 2.5 mg/kg.

Figure 14:
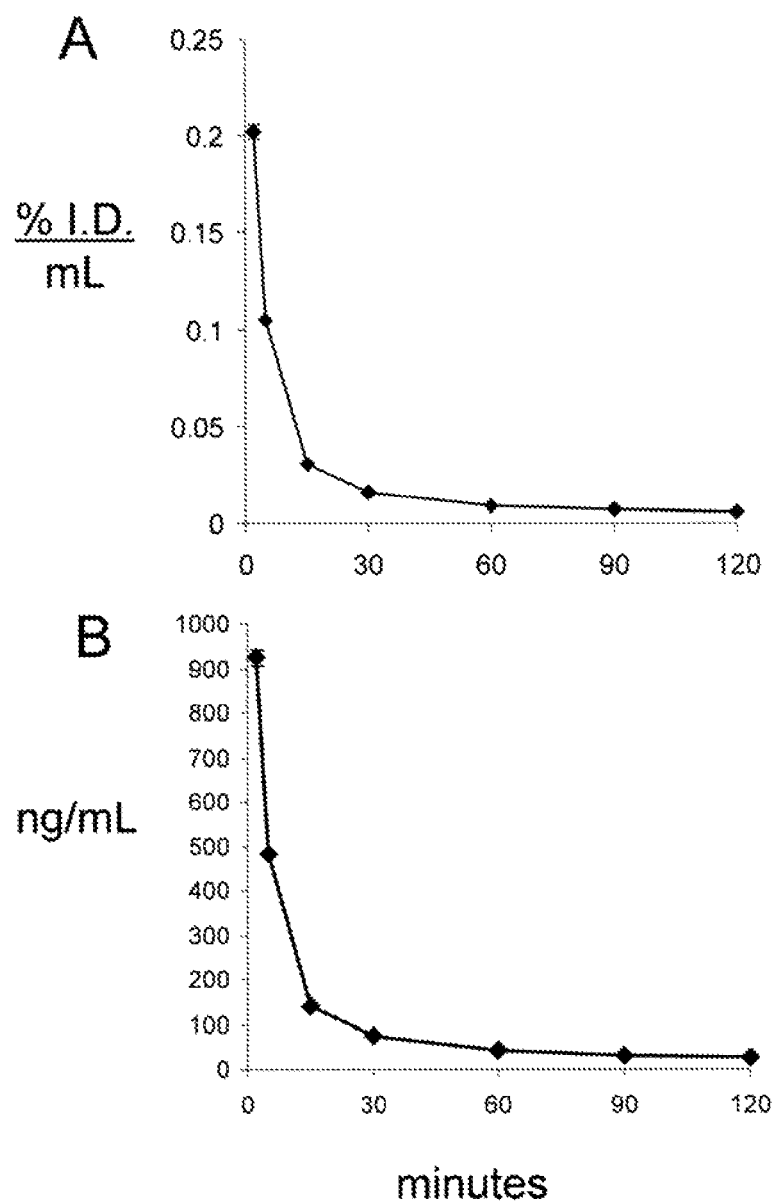
FIG. 14. Plasma concentration of the HIRMAb-ASA fusion protein in the Rhesus monkey following intravenous administration, where the concentration is represented either as a percent of injected dose (ID)/mL (A) or as ng/mL (B).

The pharmacokinetics and brain uptake of the HIRMAb-ASA fusion protein in vivo in a living monkey was evaluated with a radiolabeled form of the fusion protein. The HIRMAb-ASA fusion protein was radiolabeled with [$^{125}$I]-Bolton-Hunter reagent to a specific activity of 4.5 uCi/ug and a trichloroacetic acid (TCA) precipitability of 99%. Prior to labeling, the fusion protein was buffer exchanged with 0.01 M sodium acetate/140 mM NaCl/pH=5.5/0.001% Tween-80 and an Amicon Ultra-15 centrifugal filter unit. The labeled HIRMAb-ASA fusion protein was purified by gel filtration with a 1×28 cm column of Sephadex G-25 and an elution buffer of 0.01 M sodium acetate/140 mM NaCl/pH=5.5/0.001% Tween-80. An adult male Rhesus monkey, 8.2 kg, was investigated at a Contract Research Organization. The animal was injected intravenously (IV) with 2042 uCi of [$^{125}$I]-HIRMAb-ASA fusion protein by bolus injection over 30 seconds in the left femoral vein. The injection dose (ID) of the HIRMAb-ASA fusion protein was 55 ug/kg. The animal was anesthetized with intramuscular ketamine. Following intravenous drug administration, femoral venous plasma was obtained at 2, 5, 15, 30, 60, 90, and 120 min for determination of total plasma [$^{125}$I] radioactivity (DPM/mL) and plasma radioactivity that is precipitated by 10% cold trichloroacetic acid (TCA). The TCA-precipitable plasma concentration of the fusion protein is shown in FIG. 14 as either a percent of injected dose (ID)/mL plasma (FIG. 14A) or as ng/mL of fusion protein (FIG. 14B). The percent of total plasma radioactivity that was precipitable by TCA was 98±1%, 97±1%, 88±1%, 65±1%, 45±2%, 43±2%, and 42±2%, respectively at 2, 5, 15, 30, 60, 90, and 120 min after IV injection. The plasma profile of TCA-precipitable radioactivity was fit to a 2-exponential equation; the intercepts (A1, A2) and the slopes (k1, k2) of the two exponents of clearance were used to compute to yield the pharmacokinetics (PK) parameters shown in Table 3. The [$^{125}$I]-HIRMAb-ASA fusion protein is rapidly cleared from blood with a mean residence time (MRT) of 59±12 minutes, a systemic volume of distribution (Vss) that is 5-fold greater the central compartment volume (Vc), and a high rate of systemic clearance (CL), 3.9±0.2 mL/min/kg (Table 3). The plasma area under the concentration curve (AUC) is shown for the 120 min time period, or the predicted AUC at steady state, AUCss (Table 3).

TABLE 3

Pharmacokinetic parameters of the HIRMAb-ASA fusion protein

| parameter | units | value |
|---|---|---|
| A1 | % ID/mL | 0.243 ± 0.034 |
| A2 | % ID/mL | 0.018 ± 0.003 |
| k1 | min-1 | 0.185 ± 0.024 |
| k2 | min-1 | 0.010 ± 0.002 |
| MRT | min | 59 ± 12 |
| Vc | mL/kg | 46 ± 6 |

TABLE 3-continued

Pharmacokinetic parameters of the HIRMAb-ASA fusion protein

| parameter | units | value |
|---|---|---|
| Vss | mL/kg | 233 ± 39 |
| AUC|$^{120}$ | % ID · min/mL | 2.57 ± 0.12 |
| AUCss | % ID · min/mL | 3.10 ± 0.19 |
| AUCss | ug · min/mL | 14.2 ± 0.8 |
| CL | mL/min/kg | 3.9 ± 0.2 |

The uptake of the HIRMAb-ASA fusion protein by brain and peripheral organs in the primate was measured. The animal was euthanized at 120 minutes after fusion protein intravenous injection, and samples of major organs (heart, liver, spleen, lung, skeletal muscle, and omental fat) were removed, weighed, and processed for determination of radioactivity. The cranium was opened and the brain was removed. Samples of frontal cortical gray matter, frontal cortical white matter, cerebellar gray matter, cerebellar white matter, and choroid plexus were removed for radioactivity determination. The organ uptake of the HIRMAb-ASA fusion protein, expressed as % of injected dose (ID) per 100 gram wet organ weight, in the Rhesus monkey is listed in Table 4 for brain and peripheral organs. The major organs accounting for the removal of the HIRMAb-ASA fusion protein from plasma are liver and spleen (Table 4). The brain uptake of the HIRMAb-ASA fusion protein is 1.1±0.1% ID/100 gram brain (Table 4).

TABLE 4

Organ uptake of the HIRMAb-ASA fusion protein in the Rhesus monkey

| organ | Organ uptake (% ID/100 grams) |
|---|---|
| Frontal gray | 1.08 ± 0.09 |
| Frontal white | 0.32 ± 0.10 |
| Cerebellar gray | 0.97 ± 0.03 |
| Cerebellar white | 0.59 ± 0.07 |
| Choroid plexus | 2.19 ± 0.68 |
| liver | 22.4 ± 1.1 |
| spleen | 14.7 ± 0.3 |
| lung | 3.4 ± 0.2 |
| heart | 1.1 ± 0.1 |
| fat | 0.33 ± 0.01 |
| Skeletal muscle | 0.25 ± 0.05 |

Figure 15:
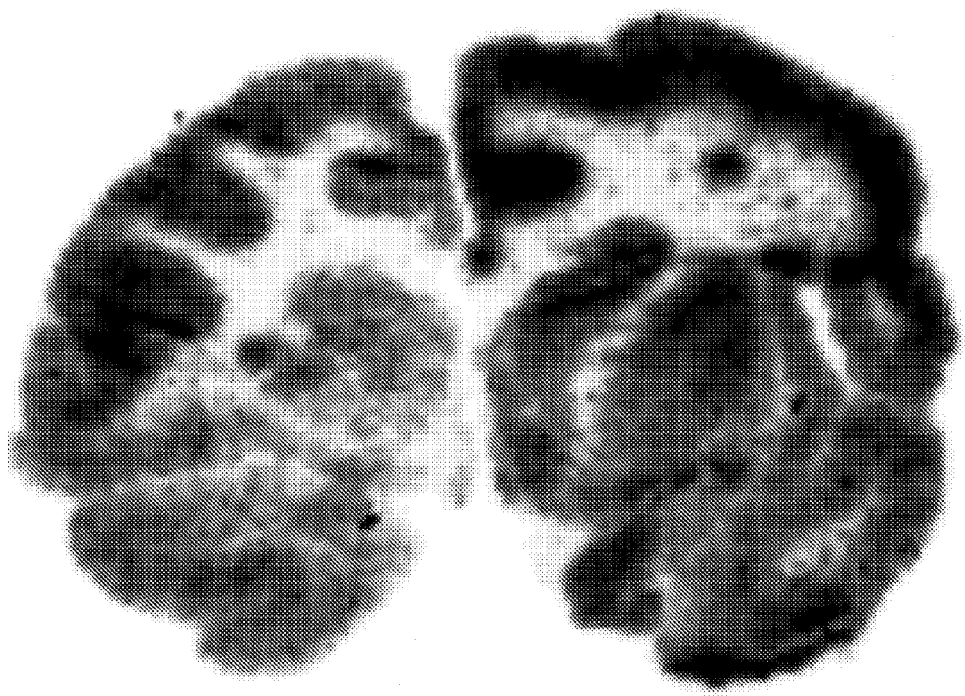
FIG. 15. Brain scan of the Rhesus monkey at 2 hours after the intravenous injection of the [$^{125}$I]-HIRMAb-ASA fusion protein shows global distribution of the fusion protein throughout the primate brain with higher uptake in gray matter as compared to white matter.

The regional uptake by brain of the HIRMAb-ASA fusion protein was confirmed by brain scanning at 2 hours after the intravenous injection of the fusion protein. After euthanasia at 2 hours, the fresh brain was removed and cut into coronal slabs, and immediately frozen in liquid nitrogen. Frozen sections (20 um) were cut with a cryostat at −15° C.; the sections were air dried and exposed to X-ray film for up to 7 days followed by x-ray film development. The films were scanned and the image was saved in Photoshop, and colorized with NIH Image software. The film autoradiography of the primate brain shows global distribution of the HIRMAb-ASA fusion protein throughout brain with higher uptake in gray matter as compared to white matter (FIG. 15). Emulsion autoradiography and light microscopy under dark field and light field illumination showed the fusion protein penetrated the BBB and was uniformly distributed to brain cells within the parenchyma of brain.

The net transport of the HIRMAb-ASA fusion protein through the brain vasculature and into brain parenchyma was confirmed with the capillary depletion method. The capillary depletion method separates the vascular tissue in brain from the post-vascular compartment (Triguero et al, 1990). Based on measurements of the specific activity of brain capillary-specific enzymes, such as γ-glutamyl transpeptidase or alkaline phosphatase, the post-vascular supernatant is >95% depleted of brain vasculature (Triguero D, Buciak J, Pardridge W M 1990. Capillary depletion method for quantification of blood-brain barrier transport of circulating peptides and plasma proteins. J. Neurochem., 54: 1882-1888). To separate the vascular and post-vascular compartments, the brain was homogenized in 8 mL cold PBS in a tissue grinder. The homogenate was supplemented with 9.4 mL cold 40% dextran (70 kDa), and an aliquot of the homogenate was taken for radioactivity measurement. The homogenate was centrifuged at 3200 g at 4 C. for 10 min in a fixed angle rotor. The brain microvasculature quantitatively sediments as the pellet, and the post-vascular supernatant is a measure of capillary depleted brain parenchyma. The vascular pellet and supernatant were counted for $^3$H radioactivity in parallel with the homogenate. The volume of distribution (VD) was determined for each of the 3 fractions from the ratio of total [$^{125}$I] radioactivity in the brain fraction (DPM/gram brain) divided by the total [$^{125}$I] radioactivity in the 120 min terminal plasma (DPM/uL plasma). The percent of radioactivity in the post-vascular supernatant that was precipitable with 10% cold TCA was determined Plasma and tissue samples were analyzed for $^{125}$I radioactivity with a gamma counter. The VD of the HIRMAb-ASA fusion protein in brain homogenate at 2 hours after injection is high, 526±23 uL/gram, compared to the brain VD of a non-specific human IgG1 isotype control antibody, 20±6 ul/gram (Table 5). The brain VD of the IgG1 isotype control antibody represents the brain uptake of a molecule that is sequestered within the blood volume of brain, and which does not cross the BBB. The high brain VD for the HIRMAb-ASA fusion protein indicates the fusion protein is either sequestered by the brain vasculature, or has penetrated the BBB and entered brain parenchyma. The VD of the HIRMAb-ASA fusion protein in the post-vascular supernatant, 341±33 uL/gram, is greater than the VD of the HIRMAb-ASA fusion protein in the vascular pellet of brain, 277±30 uL/gram (Table 5), which indicates that the majority of the HIRMAb-ASA fusion protein has traversed the BBB and penetrated the brain parenchyma. The radioactivity in the post-vascular supernatant represents intact HIRMAb-ASA fusion protein, and not labeled metabolites, as the TCA precipitation of the post-vascular supernatant radioactivity is 95.2±1.4% (Table 5).

TABLE 5

Capillary depletion analysis for brain uptake of the HIRMAb-ASA fusion protein

| Molecule | Brain fraction | VD (µL/g) |
|---|---|---|
| HIRMAb-ASA fusion protein | Brain homogenate | 526 ± 23 |
| | Post-vascular supernatant | 341 ± 33 |
| | Vascular pellet | 277 ± 30 |
| Human IgG1 isotype control | Brain homogenate | 20 ± 6 |

At 120 minutes after IV injection of the [$^{125}$I]-HIRMAb-ASA fusion protein, the plasma radioactivity is 42±2% TCA-precipitable, whereas the radioactivity in the post-vascular supernatant of brain is 95±1% TCA-precipitable. This finding means that radioactivity that distributes to brain from blood is the intact HIRMAb-ASA fusion protein, and not radiolabeled metabolites. The results of the capillary depletion method confirm the results of the emulsion autoradiography and demonstrated the fusion protein penetrates the BBB at the brain microvasculature and is delivered to brain cells in the parenchyma of brain.

What is claimed:

1. A fusion antibody comprising: (a) a fusion protein comprising the amino acid sequences of an immunoglobulin heavy chain and an arylsulfatase A monomer (ASA), and (b) an immunoglobulin light chain; wherein the fusion antibody crosses the blood brain barrier (BBB).

2. The fusion antibody of claim 1, wherein the amino acid sequence of the arylsulfatase A is covalently linked to the carboxy terminus of the amino acid sequence of the immunoglobulin heavy chain.

3. The fusion antibody of claim 1, wherein the fusion antibody is post-translationally modified by a sulfatase modifying factor type 1 (SUMF1).

4. The fusion antibody of claim 1, wherein the fusion antibody comprises a formylglycine.

5. The fusion antibody of claim 1, wherein the fusion protein further comprises a linker between the amino acid sequence of the arylsulfatase A and the carboxy terminus of the amino acid sequence of the immunoglobulin heavy chain.

6. The fusion antibody of claim 1, wherein the arylsulfatase A specific activity of the fusion antibody is at least about 10 units/mg of protein.

7. The fusion antibody of claim 1, wherein the ASA retains at least 20% of its activity compared to its activity as a separate entity.

8. The fusion antibody of claim 1, wherein the ASA and the immunoglobulin each retains at least 20% of its activity, on a molar basis, compared to its activity as a separate entity.

9. The fusion antibody of claim 1, wherein the immunoglobulin heavy chain is an immunoglobulin heavy chain of IgG.

10. The fusion antibody of claim 1, wherein the immunoglobulin heavy chain comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

11. The fusion antibody of claim 1, wherein the immunoglobulin light chain is an immunoglobulin light chain of kappa class.

12. The fusion antibody of claim 1, wherein the immunoglobulin light chain is an immunoglobulin light chain of lambda class.

13. The fusion antibody of claim 1, wherein the immunoglobulin light chain comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

14. The fusion antibody of claim 1, wherein the fusion antibody crosses the BBB by binding an endogenous BBB receptor-mediated transport system.

15. The fusion antibody of claim 1, wherein the fusion antibody crosses the BBB by binding an endogenous BBB receptor selected from the group consisting of the insulin receptor, transferrin receptor, leptin receptor, lipoprotein receptor, and the IGF receptor.

16. The fusion antibody of claim 1, wherein the fusion antibody crosses the BBB by binding an insulin receptor.

17. A pharmaceutical composition comprising a therapeutically effective amount of a fusion antibody of claim 1, and a pharmaceutically acceptable excipient.

18. An isolated polynucleotide encoding the fusion antibody of claim 1.

19. The fusion antibody of claim 1, wherein the fusion antibody catalyzes hydrolysis of 2-sulfate groups of cerebroside sulfate esters and sulfatide sphingolipids.

20. The fusion antibody of claim 1, wherein the fusion protein comprises an amino acid sequence that is at least 80% identical to SEQ ID NO:10.

21. The isolated polynucleotide of claim 18, wherein the isolated polynucleotide comprises the nucleic acid sequence of SEQ ID NO:14.

22. A vector comprising the isolated polynucleotide of claim 18.

23. The vector of claim 22 comprising the nucleic acid sequence of SEQ ID NO:14.

24. A host cell comprising the vector of claim 22.

25. The host cell of claim 24, wherein the host cell is a Chinese Hamster Ovary (CHO) cell.

26. A fusion antibody comprising: (a) a fusion protein comprising the amino acid sequences of an immunoglobulin heavy chain and an arylsulfatase A monomer, and (b) an immunoglobulin light chain; wherein the fusion antibody crosses the blood brain barrier (BBB), wherein the amino acid sequence of the arylsulfatase A is covalently linked to the carboxy terminus of the amino acid sequence of the immunoglobulin heavy chain.

* * * * *

SEQUENCE LISTING

<160> NUMBER OF SEQ ID NOS: 16

<210> SEQ ID NO 1
<211> LENGTH: 10
<212> TYPE: PRT
<213> ORGANISM: Artificial sequence
<220> FEATURE:
<223> OTHER INFORMATION: Synthetic protein

<400> SEQUENCE: 1

Gly Tyr Thr Phe Thr Asn Tyr Asp Ile His
1               5                   10

<210> SEQ ID NO 2
<211> LENGTH: 17
<212> TYPE: PRT
<213> ORGANISM: Artificial sequence
<220> FEATURE:
<223> OTHER INFORMATION: Synthetic protein

<400> SEQUENCE: 2

Trp Ile Tyr Pro Gly Asp Gly Ser Thr Lys Tyr Asn Glu Lys Phe Lys
1               5                   10                  15

Gly

<210> SEQ ID NO 3
<211> LENGTH: 4
<212> TYPE: PRT
<213> ORGANISM: Artificial sequence

```
<220> FEATURE:
<223> OTHER INFORMATION: Synthetic protein

<400> SEQUENCE: 3

Glu Trp Ala Tyr
1

<210> SEQ ID NO 4
<211> LENGTH: 11
<212> TYPE: PRT
<213> ORGANISM: Artificial sequence
<220> FEATURE:
<223> OTHER INFORMATION: Synthetic protein

<400> SEQUENCE: 4

Arg Ala Ser Gln Asp Ile Gly Gly Asn Leu Tyr
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic protein

<400> SEQUENCE: 5

Ala Thr Ser Ser Leu Asp Ser
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic protein

<400> SEQUENCE: 6

Leu Gln Tyr Ser Ser Ser Pro Trp Thr
1               5

<210> SEQ ID NO 7
<211> LENGTH: 462
<212> TYPE: PRT
<213> ORGANISM: Artificial sequence
<220> FEATURE:
<223> OTHER INFORMATION: Synthetic protein

<400> SEQUENCE: 7

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
                20                  25                  30

Pro Gly Ala Leu Val Lys Ile Ser Cys Lys Ala Ser Gly Tyr Thr Phe
            35                  40                  45

Thr Asn Tyr Asp Ile His Trp Val Lys Gln Arg Pro Gly Gln Gly Leu
        50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125
```

```
Thr Val Ser Ala Ala Ser Thr Lys Gly Pro Ser Val Phe Pro Leu Ala
            130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 8
<211> LENGTH: 234
<212> TYPE: PRT
<213> ORGANISM: Artificial sequence
<220> FEATURE:
<223> OTHER INFORMATION: Synthetic protein

<400> SEQUENCE: 8

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30
```

Ala Ser Leu Gly Glu Arg Val Ser Leu Thr Cys Arg Ala Ser Gln Asp
            35                  40                  45

Ile Gly Gly Asn Leu Tyr Trp Leu Gln Gln Gly Pro Asp Gly Thr Ile
        50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Thr Lys Met Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 9
<211> LENGTH: 489
<212> TYPE: PRT
<213> ORGANISM: Artificial sequence
<220> FEATURE:
<223> OTHER INFORMATION: Synthetic protein

<400> SEQUENCE: 9

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Cys Thr Pro Ser Arg Ala Ala Leu Leu Thr Gly Arg Leu Pro
50                  55                  60

Val Arg Met Gly Met Tyr Pro Gly Val Leu Val Pro Ser Ser Arg Gly
65                  70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
            115                 120                 125

Ile Pro Tyr Ser His Asp Gln Gly Pro Cys Gln Asn Leu Thr Cys Phe
        130                 135                 140

Pro Pro Ala Thr Pro Cys Asp Gly Gly Cys Asp Gln Gly Leu Val Pro
145                 150                 155                 160

Ile Pro Leu Leu Ala Asn Leu Ser Val Glu Ala Gln Pro Pro Trp Leu

```
                    165                 170                 175
Pro Gly Leu Glu Ala Arg Tyr Met Ala Phe Ala His Asp Leu Met Ala
            180                 185                 190

Asp Ala Gln Arg Gln Asp Arg Pro Phe Phe Leu Tyr Tyr Ala Ser His
        195                 200                 205

His Thr His Tyr Pro Gln Phe Ser Gly Gln Ser Phe Ala Glu Arg Ser
    210                 215                 220

Gly Arg Gly Pro Phe Gly Asp Ser Leu Met Glu Leu Asp Ala Ala Val
225                 230                 235                 240

Gly Thr Leu Met Thr Ala Ile Gly Asp Leu Gly Leu Leu Glu Glu Thr
                245                 250                 255

Leu Val Ile Phe Thr Ala Asp Asn Gly Pro Glu Thr Met Arg Met Ser
            260                 265                 270

Arg Gly Gly Cys Ser Gly Leu Leu Arg Cys Gly Lys Gly Thr Thr Tyr
        275                 280                 285

Glu Gly Gly Val Arg Glu Pro Ala Leu Ala Phe Trp Pro Gly His Ile
    290                 295                 300

Ala Pro Gly Val Thr His Glu Leu Ala Ser Ser Leu Asp Leu Leu Pro
305                 310                 315                 320

Thr Leu Ala Ala Leu Ala Gly Ala Pro Leu Pro Asn Val Thr Leu Asp
                325                 330                 335

Gly Phe Asp Leu Ser Pro Leu Leu Leu Gly Thr Gly Lys Ser Pro Arg
            340                 345                 350

Gln Ser Leu Phe Phe Tyr Pro Ser Tyr Pro Asp Glu Val Arg Gly Val
        355                 360                 365

Phe Ala Val Arg Ser Gly Lys Tyr Lys Ala His Phe Phe Thr Gln Gly
    370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
                405                 410                 415

Pro Gly Glu Asn Tyr Asn Leu Leu Gly Gly Val Ala Gly Ala Thr Pro
            420                 425                 430

Glu Val Leu Gln Ala Leu Lys Gln Leu Gln Leu Leu Lys Ala Gln Leu
        435                 440                 445

Asp Ala Ala Val Thr Phe Gly Pro Ser Gln Val Ala Arg Gly Glu Asp
    450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
                485

<210> SEQ ID NO 10
<211> LENGTH: 953
<212> TYPE: PRT
<213> ORGANISM: Artificial sequence
<220> FEATURE:
<223> OTHER INFORMATION: Synthetic protein

<400> SEQUENCE: 10

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45
```

```
Thr Asn Tyr Asp Ile His Trp Val Lys Gln Arg Pro Gly Gln Gly Leu
    50                  55                  60
Glu Trp Ile Gly Trp Ile Tyr Pro Gly Asp Gly Ser Thr Lys Tyr Asn
65                  70                  75                  80
Glu Lys Phe Lys Gly Lys Ala Thr Leu Thr Ala Asp Lys Ser Ser Ser
                85                  90                  95
Thr Ala Tyr Met His Leu Ser Ser Leu Thr Ser Glu Lys Ser Ala Val
                100                 105                 110
Tyr Phe Cys Ala Arg Glu Trp Ala Tyr Trp Gly Gln Gly Thr Leu Val
            115                 120                 125
Thr Val Ser Ala Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Ser Ser Ser
450                 455                 460
Arg Pro Pro Asn Ile Val Leu Ile Phe Ala Asp Asp Leu Gly Tyr Gly
```

```
                465                 470                 475                 480
Asp Leu Gly Cys Tyr Gly His Pro Ser Ser Thr Thr Pro Asn Leu Asp
                    485                 490                 495

Gln Leu Ala Ala Gly Gly Leu Arg Phe Thr Asp Phe Tyr Val Pro Val
                500                 505                 510

Ser Leu Cys Thr Pro Ser Arg Ala Ala Leu Leu Thr Gly Arg Leu Pro
            515                 520                 525

Val Arg Met Gly Met Tyr Pro Gly Val Leu Val Pro Ser Ser Arg Gly
        530                 535                 540

Gly Leu Pro Leu Glu Glu Val Thr Val Ala Glu Val Leu Ala Ala Arg
545                 550                 555                 560

Gly Tyr Leu Thr Gly Met Ala Gly Lys Trp His Leu Gly Val Gly Pro
                565                 570                 575

Glu Gly Ala Phe Leu Pro Pro His Gln Gly Phe His Arg Phe Leu Gly
                580                 585                 590

Ile Pro Tyr Ser His Asp Gln Gly Pro Cys Gln Asn Leu Thr Cys Phe
            595                 600                 605

Pro Pro Ala Thr Pro Cys Asp Gly Gly Cys Asp Gln Gly Leu Val Pro
        610                 615                 620

Ile Pro Leu Leu Ala Asn Leu Ser Val Glu Ala Gln Pro Pro Trp Leu
625                 630                 635                 640

Pro Gly Leu Glu Ala Arg Tyr Met Ala Phe Ala His Asp Leu Met Ala
                645                 650                 655

Asp Ala Gln Arg Gln Asp Arg Pro Phe Phe Leu Tyr Tyr Ala Ser His
                660                 665                 670

His Thr His Tyr Pro Gln Phe Ser Gly Gln Ser Phe Ala Glu Arg Ser
            675                 680                 685

Gly Arg Gly Pro Phe Gly Asp Ser Leu Met Glu Leu Asp Ala Ala Val
        690                 695                 700

Gly Thr Leu Met Thr Ala Ile Gly Asp Leu Gly Leu Leu Glu Glu Thr
705                 710                 715                 720

Leu Val Ile Phe Thr Ala Asp Asn Gly Pro Glu Thr Met Arg Met Ser
                725                 730                 735

Arg Gly Gly Cys Ser Gly Leu Leu Arg Cys Gly Lys Gly Thr Thr Tyr
                740                 745                 750

Glu Gly Gly Val Arg Glu Pro Ala Leu Ala Phe Trp Pro Gly His Ile
            755                 760                 765

Ala Pro Gly Val Thr His Glu Leu Ala Ser Ser Leu Asp Leu Leu Pro
        770                 775                 780

Thr Leu Ala Ala Leu Ala Gly Ala Pro Leu Pro Asn Val Thr Leu Asp
785                 790                 795                 800

Gly Phe Asp Leu Ser Pro Leu Leu Gly Thr Gly Lys Ser Pro Arg
                805                 810                 815

Gln Ser Leu Phe Phe Tyr Pro Ser Tyr Pro Asp Glu Val Arg Gly Val
                820                 825                 830

Phe Ala Val Arg Ser Gly Lys Tyr Lys Ala His Phe Phe Thr Gln Gly
            835                 840                 845

Ser Ala His Ser Asp Thr Thr Ala Asp Pro Ala Cys His Ala Ser Ser
        850                 855                 860

Ser Leu Thr Ala His Glu Pro Pro Leu Leu Tyr Asp Leu Ser Lys Asp
865                 870                 875                 880

Pro Gly Glu Asn Tyr Asn Leu Leu Gly Gly Val Ala Gly Ala Thr Pro
                885                 890                 895
```

```
Glu Val Leu Gln Ala Leu Lys Gln Leu Gln Leu Lys Ala Gln Leu
                900                 905                 910

Asp Ala Ala Val Thr Phe Gly Pro Ser Gln Val Ala Arg Gly Glu Asp
            915                 920                 925

Pro Ala Leu Gln Ile Cys Cys His Pro Gly Cys Thr Pro Arg Pro Ala
        930                 935                 940

Cys Cys His Cys Pro Asp Pro His Ala
945                 950

<210> SEQ ID NO 11
<211> LENGTH: 22
<212> TYPE: DNA
<213> ORGANISM: Artificial sequence
<220> FEATURE:
<223> OTHER INFORMATION: Synthetic DNA

<400> SEQUENCE: 11
cccgtccgcc caacatcgtg ct                                          22

<210> SEQ ID NO 12
<211> LENGTH: 24
<212> TYPE: DNA
<213> ORGANISM: Artificial sequence
<220> FEATURE:
<223> OTHER INFORMATION: Synthetic DNA

<400> SEQUENCE: 12
tcaggcatgg ggatctgggc aatg                                        24

<210> SEQ ID NO 13
<211> LENGTH: 714
<212> TYPE: DNA
<213> ORGANISM: Artificial sequence
<220> FEATURE:
<223> OTHER INFORMATION: Synthetic DNA

<400> SEQUENCE: 13
gccgccacca tggagacccc cgcccagctg ctgttcctgt tgctgctttg gcttccagat    60
actaccggcg acatccagat gacccagtct ccatcctcct tatctgcctc tctgggagaa   120
agagtcagtc tcacttgtcg ggcaagtcag gacattggtg gtaacttata ctggcttcag   180
cagggaccag atggaactat taaacgcctg atctacgcca catccagttt agattctggt   240
gtccccaaaa ggttcagtgg cagtaggtct gggtcagatt attctctcac catcagcagc   300
cttgagtctg aagattttgt agactattac tgtctacagt attctagttc ccgtggacg    360 ttcggtggag gcacaaagct ggaaataaaa cgaactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttag         714

<210> SEQ ID NO 14
<211> LENGTH: 2871
<212> TYPE: DNA
<213> ORGANISM: Artificial sequence
<220> FEATURE:
<223> OTHER INFORMATION: Synthetic DNA

<400> SEQUENCE: 14
```

```
gccgccacca tggactggac ctggagggtg ttctgcctgc ttgcagtggc ccccggagcc      60
cacagccagg ttcagctgca gcagtctgga cctgagctgg tgaagcctgg ggctttagtg     120
aagatatcct gcaaggcttc tggttacacc ttcacaaact acgatataca ctgggtgaag     180
cagaggcctg acagggact tgagtggatt ggatggattt atcctggaga tggtagtact      240
aagtacaatg agaaattcaa gggcaaggcc acactgactg cagacaaatc ctccagcaca     300
gcctacatgc acctcagcag cctgacttct gagaaatctg cagtctattt ctgtgcaaga     360
gagtgggctt actggggcca agggactctg gtcactgtct ctgcagctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagaaagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caaagggcag    1080
ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctcctg gtagtagttc ccgtccgccc aacatcgtgc tgatctttgc cgacgacctc    1440
ggctatgggg acctgggctg ctatgggcac cccagctcta ccactcccaa cctgaccag    1500
ctggcggcgg agggctgcg gttcacagac ttctacgtgc ctgtgtctct gtgcacaccc    1560
tctagggccg ccctcctgac cggccggctc ccggttcgga tgggcatgta ccctggcgtc    1620
ctggtgccca gctcccgggg gggcctgccc ctggaggagg tgaccgtggc cgaagtcctg    1680
gctgcccgag ctacctcac aggaatggcc ggcaagtggc accttgggt ggggcctgag     1740
ggggccttcc tgcccccca tcagggcttc catcgatttc taggcatccc gtactcccac    1800
gaccagggcc cctgccagaa cctgacctgc ttccgccgg ccactccttg cgacggtggc    1860
tgtgaccagg gcctggtccc catcccactg ttggccaacc tgtccgtgga ggcgcagccc    1920
ccctggctgc ccggactaga ggcccgctac atggctttcg cccatgacct catggccgac    1980
gcccagcgcc aggatcgccc cttcttcctg tactatgcct ctcaccacac ccactaccct    2040
cagttcagtg gcagagctt tgcagagcgt tcaggccgcg ggccatttgg ggactccctg    2100
atggagctgg atgcagctgt ggggacctg atgacagcca taggggacct ggggctgctt    2160
gaagagacgc tggtcatctt cactgcagac aatggacctg agaccatgcg tatgtcccga    2220
ggcggctgct ccggtctctt gcggtgtgga aagggaacga cctacgaggg cggtgtccga    2280
gagcctgcct tggccttctg gcaggtcat atcgctcccg gcgtgaccca cgagctggcc    2340
agctccctgg acctgctgcc taccctggca gccctggctg gggcccact gcccaatgtc    2400
```

```
acctggatg ctttgacct cagccccctg ctgctgggca caggcaagag ccctcggcag    2460
tctctcttct tctacccgtc ctacccagat gaggtccgtg gggttttgc tgtgcggagt    2520 ggaaagtaca aggctcactt cttcacccag ggctctgccc acagtgatac cactgcagac    2580
cctgcctgcc acgcctccag ctctctgact gctcatgagc ccccgctgct ctatgacctg    2640
tccaaggacc ctggtgagaa ctacaacctg ctgggggtg tggccggggc cacccccagag   2700 gtgctgcaag ccctgaaaca gcttcagctg ctcaaggccc agttagacgc agctgtgacc    2760
ttcggcccca gccaggtggc ccggggcgag gaccccgccc tgcagatctg ctgtcatcct    2820
ggctgcaccc cccgcccagc ttgctgccat tgcccagatc cccatgcctg a             2871
```

<210> SEQ ID NO 15
<211> LENGTH: 573
<212> TYPE: DNA
<213> ORGANISM: Artificial sequence
<220> FEATURE:
<223> OTHER INFORMATION: Synthetic DNA

<400> SEQUENCE: 15

```
gccgccacca tggttcgacc attgaactgc atcgtcgccg tgtcccaaaa tatggggatt      60
ggcaagaacg gagacctacc ctggcctccg ctcaggaacg agttcaagta cttccaaaga    120
atgaccacaa cctcttcagt ggaaggtaaa cagaatctgg tgattatggg taggaaaacc    180
tggttctcca ttcctgagaa gaatcgacct ttaaaggaca gaattaatat agttctcagt    240
agagaactca agaaccacc acgaggagct cattttcttg ccaaaagttt ggatgatgcc     300
ttaagactta ttgaacaacc ggaattggca agtaaagtag acatggtttg atagtcgga    360 ggcagttctg tttaccagga agccatgaat caaccaggcc acctcagact ctttgtgaca    420
aggatcatgc aggaatttga agtgacacg ttttccag aaattgattt ggggaaatat       480
aaacttctcc cagaataccc aggcgtcctc tctgaggtcc aggaggaaaa aggcatcaag   540
tataagtttg aagtctacga agaaagac taa                                   573
```

<210> SEQ ID NO 16
<211> LENGTH: 187
<212> TYPE: PRT
<213> ORGANISM: Artificial sequence
<220> FEATURE:
<223> OTHER INFORMATION: Synthetic protein

<400> SEQUENCE: 16

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

```
                    -continued
Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
                180                 185
```